United States Patent [19]
Sen et al.

[11] Patent Number: 5,639,614
[45] Date of Patent: Jun. 17, 1997

[54] GENE MUTATION IN PATIENTS WITH IDIOPATHIC DILATED CARDIOMYOPATHY

[75] Inventors: Luyi Sen, Stevenson Ranch; Kenneth D. Philipson, Pacific Palisades; Aldons Jake Lusis, Los Angeles, all of Calif.

[73] Assignee: The Regents of the University of California, Oakland, Calif.

[21] Appl. No.: 480,481

[22] Filed: Jun. 7, 1995

[51] Int. Cl.$^6$ .............................. C12Q 1/68; C07H 21/04; C12P 19/34

[52] U.S. Cl. .......................... 435/6; 435/91.2; 536/23.5; 536/24.31; 536/24.33; 935/8; 935/9; 935/10; 935/77; 935/78

[58] Field of Search ................... 435/6, 91.2; 536/23.5, 536/24.31, 24.33; 935/8, 9, 10, 77, 78

[56] References Cited

U.S. PATENT DOCUMENTS 4,683,195  7/1987  Mullis .......................................... 435/6

OTHER PUBLICATIONS

Brillantes et al, Circulation Research (1992) 71:18–26.

Otsu et al, Journal Biological Chemistry (1990) 265; 13472–13483.

Chen, et al., "Characterization of a $Ca^{2+}$ Binding and Regulatory Site in the $Ca^{2+}$ Release Channel (Ryanodine Receptor) of Rabbit Skeletal Muscle Sarcoplasmic Reticulum", The Journal of Biological Chemistry, vol. 267, No. 32, pp. 23318–23326, Nov. 15, 1992.

Fujii, et al., "Identification of a Mutation in Porcine Ryanodine Receptor Associated with Malignant hyperthermia", Science, vol. 253, pp. 448–451, Jul. 26, 1991.

Sen, et al., "Enhanced $\alpha_1$–Adrenergic Responsiveness in Cardiomyopathic Hamster Cardiac Myocytes: Relation to the Expression of Pertussis Toxin–Sensitive G Protein and $\alpha_1$–Adrenergic Receptors", Circulation Research, vol. 67, No. 5, pp. 1182–1192, Nov. 1990.

Sen, et al., "Inotropic and Calcium Kinetic Effects of Calcium Channel Agonist and Antagonist in Isolated Cardiac Myocytes From Cardiomyopathic Hamsters", Circulation Research, vol. 67, No. 3, pp. 599–608, Sep. 1990.

Sen, et al., "Myocyte Structure, Function, and Calcium Kinetics in the Cardiomyopathic Hamster Heart", The American Physiological Society, pp. H1533–H1543, 1990.

Sen, et al., "T–Type $Ca^{2+}$ Channels Are Abnormal in Genetically Determined Cardiomyopathic Hamster Hearts", Circulation Research, vol. 75, No. 1, pp. 149–155, Jul. 1994.

Witcher, et al., "Unique Phosphorylation Site on the Cardiac Ryanodine Receptor Regulates Calcium Channel Activity", The Journal of Biological Chemistry, vol. 266, No. 17, pp. 11144–11152, Jun. 15, 1991.

Tunwell, et al., "Expression Studies With cDNAs Encoding the Human Cardiac Ryanodine Receptor–Calcium Release Channel", Ryanodine Receptor: Molecular Biology and Biochemistry, p. A52, M–Pos136.

Takekura, et al., "Peripheral Couplings and Triads Lack Feet and Tetrads in Dyspedic Mice With a Targeted Mutation of the Gene for Skeletal Muscle Ryanodine Receptor", Ryanodine Receptor: Structure and Function, p. A127, Tu–AM–E1.

Sitsapesan, et al., "Luminal $Ca^{2+}$ Regulates the Open Probability of Skeletal SR $Ca^{2+}$–Release Channels Activated by ATP and cADP–Ribose", Ryanodine Receptor: Structure and Function, p. A127, Tu–AM–E3.

(List continued on next page.)

Primary Examiner—Carl J. Myers
Attorney, Agent, or Firm—Knobbe Martens Olson & Bear, LLP

[57] ABSTRACT

A genetic mutation within the SR calcium release channel provides a test for susceptibility to idiopathic dilated cardiomyopathy. The test detects the presence of the mutation in a sample of nucleic acids obtained from the individual being tested. Restriction fragment length polymorphism is one technique which can be used in the test.

15 Claims, 7 Drawing Sheets

OTHER PUBLICATIONS

Ondrias, et al., "Single Channel Properties of the Full Length and Truncated Cloned Expressed by Anodine Receptor", Ryanodine Receptor: Structure and Function, p. A127, Tu–AM–E5.

Chen, et al., "Rectification of the Calcium Release Channel of Skeletal Muscle Sarcoplasmic Reticulum (Ryanodine Receptor) by FK506 Binding Protein 12", Ryanodine Receptor: Structure and Function, p. A127, Tu–AM–E2.

Kobrinsky, et al., "Functional Properties of the Skeletal Muscle Ryanodine Receptor Expressed in *Xenopus Oocytes*", Ryanodine Receptor: Structure and Function, p. A127, Tu–AM–E4.

Guo, et al., "Association of Triadin with the Ryanodine Receptor and Calsequestrin in the Lumen of Sarcoplasmic Reticulum", Ryanodine Receptor: Structure and Function, p. A127, Tu–AM–E6.

SEQUENCE LISTING ( 1 ) GENERAL INFORMATION:

( i i i ) NUMBER OF SEQUENCES: 6

-continued ( 2 ) INFORMATION FOR SEQ ID NO:1:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( i x ) FEATURE:
        ( A ) NAME/KEY: Other
        ( B ) LOCATION: 1...1
        ( D ) OTHER INFORMATION: Position 1 corresponds to
            7987 of the rabbit cDNA homolog ( x i ) SEQUENCE DESCRIPTION: SEQ ID NO:1:

TTCAAACTGG CACTGCCTTG CCTGAGTGCC GTTGC            35

( 2 ) INFORMATION FOR SEQ ID NO:2:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( v ) FRAGMENT TYPE:

( v i ) ORIGINAL SOURCE:

( x i ) SEQUENCE DESCRIPTION: SEQ ID NO:2:

AAGTTTGCAG AATAGGCTAG TCACCATTTC            30

( 2 ) INFORMATION FOR SEQ ID NO:3:

( i ) SEQUENCE CHARACTERISTICS:
        ( A ) LENGTH: 1050 base pairs
        ( B ) TYPE: nucleic acid
        ( C ) STRANDEDNESS: double
        ( D ) TOPOLOGY: linear ( i i ) MOLECULE TYPE: Genomic DNA ( i i i ) HYPOTHETICAL: NO ( i v ) ANTI-SENSE: NO ( v ) FRAGMENT TYPE:

( v i ) ORIGINAL SOURCE:

( i x ) FEATURE:
        ( A ) NAME/KEY: Other
        ( B ) LOCATION: 1...1
        ( D ) OTHER INFORMATION: Position 1 corresponds to
            7987 of the rabbit cDNA homolog ( x i ) SEQUENCE DESCRIPTION: SEQ ID NO:3:

TTCAAACTGG CACTGCCTTG CCTGAGTGCC GTTGCGGGAG CTTTGCCTCC AGACTACATG    60

| GAATCAAATT | ATGTCAGTAT | GATGGAAAAA | CAGTCATCAA | TGGATTCTGA | AGGGAACTTT | 120 |
| GAATCAAATT | ATGTCAGTAT | GATGGAAAAA | CAGTCATCAA | TGGATTCTGA | AGGGAACTTT | 120 |
| AACCCACAAC | CTGTTGATAC | CTCAAATATT | ATAATTCCTG | AGAAGTTGGA | ATACTTCATT | 180 |
| AACAAATATG | CAGAACATTC | TCATGACAAA | TGGTCAATGG | ACAAGTTAGC | AAATGGATGG | 240 |
| ATTTATGGAG | AAATATATTC | AGACTCCTCC | AAGATTCAAC | CCTTGATGAA | ACCATATAAA | 300 |
| CTATTATCTG | AAAAGGAAAA | AGAAATTTAT | CGCTGGCCAA | TCAAAGAATC | TCTCAAAACT | 360 |
| ATGTTGGCTT | GGGGTTGGAG | GATTGAAAGA | ACCCAGAAG | GAGACAGCAT | GGCCCTTTAT | 420 |
| AACCGAACTC | GTCGTATTTC | TCAGACAAGC | CAGGTTTCTG | TAGATGCTGC | CCATGGTTAT | 480 |
| AGTCCCCGAG | CCATTGACAT | GAGCAATGTT | ACACTATCCA | GAGACCTGCA | TGCTATGGCA | 540 |
| GAAATGATGG | CTGAAAACTA | TCATAACATA | TGGGCAAAGA | AAAGAAACT | GGAGTTGGAG | 600 |
| TCTAAAGGAG | GTGGAAACCA | TCCTCTGCTG | GTACCCTATG | ATACGCTGAC | AGCCAAAGAG | 660 |
| AAAGCCAAGG | ATAGGGAAAA | GGCACAGGAC | ATCCTCAAGT | TCTTGCAGAT | CAATGGATAT | 720 |
| GCTGTATCCA | GAGGATTCAA | GGACCTGGAA | CTGGACACAC | CTTCCATTGA | GAAGCGTTTC | 780 |
| GCCTATAGTT | TCCTCCAGCA | ACTTATCCGC | TATGTGGATG | AAGCTCATCA | GTACATCCTG | 840 |
| GAGTTTGATG | GTGGCAGCAG | AAGCAAAGGA | GAACATTTCC | CTTATGAACA | AGAAATCAAG | 900 |
| TTCTTTGCAA | AAGTCGTTCT | ACCTTTAATT | GATCAGTATT | TCAAAAACCA | TCGTTTATAC | .960 |
| TTCTTATCTG | CAGCAAGCAG | ACCTCTCTGC | TCTGGAGGGC | ATGCATCAAA | CAAAGAGAAG | 1020 |
| GAAATGGTGA | CTAGCCTATT | CTGCAAACTT | | | | 1050 |

( 2 ) INFORMATION FOR SEQ ID NO:4:

( i ) SEQUENCE CHARACTERISTICS:
        ( A ) LENGTH: 1050 base pairs
        ( B ) TYPE: nucleic acid
        ( C ) STRANDEDNESS: double
        ( D ) TOPOLOGY: linear ( i i ) MOLECULE TYPE: Genomic DNA ( i i i ) HYPOTHETICAL: NO ( i v ) ANTI-SENSE: NO ( v ) FRAGMENT TYPE:

( v i ) ORIGINAL SOURCE:

( i x ) FEATURE:
        ( A ) NAME/KEY: Other
        ( B ) LOCATION: 380...380
        ( D ) OTHER INFORMATION: Position distinguishes idiopathic
            dilated cardiomyopathy
        ( A ) NAME/KEY: Other
        ( B ) LOCATION: 776...776
        ( D ) OTHER INFORMATION: Position distinguishes idiopathic
            dilated cardiomyopathy
        ( A ) NAME/KEY: Other
        ( B ) LOCATION: 1...1
        ( D ) OTHER INFORMATION: Position 1 corresponds to
            7987 of the rabbit cDNA homolog ( x i ) SEQUENCE DESCRIPTION: SEQ ID NO:4:

| TTCAAACTGG | CACTGCCTTG | CCTGAGTGCC | GTTGCGGGAG | CTTTGCCTCC | AGACTACATG | 60 |
| GAATCAAATT | ATGTCAGTAT | GATGGAAAAA | CAGTCATCAA | TGGATTCTGA | AGGGAACTTT | 120 |
| AACCCACAAC | CTGTTGATAC | CTCAAATATT | ATAATTCCTG | AGAAGTTGGA | ATACTTCATT | 180 |
| AACAAATATG | CAGAACATTC | TCATGACAAA | TGGTCAATGG | ACAAGTTAGC | AAATGGATGG | 240 |
| ATTTATGGAG | AAATATATTC | AGACTCCTCC | AAGATTCAAC | CCTTGATGAA | ACCATATAAA | 300 |
| CTATTATCTG | AAAAGGAAAA | AGAAATTTAT | CGCTGGCCAA | TCAAAGAATC | TCTCAAAACT | 360 |

```
ATGTTGGCTT GGGGTTGGAA GATTGAAAGA ACCCCAGAAG GAGACAGCAT GGCCCTTTAT      420

AACCGAACTC GTCGTATTTC TCAGACAAGC CAGGTTTCTG TAGATGCTGC CCATGGTTAT      480

AGTCCCCGAG CCATTGACAT GAGCAATGTT ACACTATCCA GAGACCTGCA TGCTATGGCA      540

GAAATGATGG CTGAAAACTA TCATAACATA TGGGCAAAGA AAAGAAACT GGAGTTGGAG       600

TCTAAAGGAG GTGGAAACCA TCCTCTGCTG GTACCCTATG ATACGCTGAC AGCCAAGAG      660

AAAGCCAAGG ATAGGGAAAA GGCACAGGAC ATCCTCAAGT TCTTGCAGAT CAATGGATAT      720

GCTGTATCCA GAGGATTCAA GGACCTGGAA CTGGACACAC CTTCCATTGA GAAGCTTTTC      780

GCCTATAGTT TCCTCCAGCA ACTTATCCGC TATGTGGATG AAGCTCATCA GTACATCCTG      840

GAGTTTGATG GTGGCAGCAG AAGCAAGGA GAACATTTCC CTTATGAACA AGAAATCAAG      900

TTCTTTGCAA AAGTCGTTCT ACCTTTAATT GATCAGTATT TCAAAAACCA TCGTTTATAC      960

TTCTTATCTG CAGCAAGCAG ACCTCTCTGC TCTGGAGGGC ATGCATCAAA CAAAGAGAAG     1020

GAAATGGTGA CTAGCCTATT CTGCAAACTT                                     1050
```

( 2 ) INFORMATION FOR SEQ ID NO:5:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( i x ) FEATURE:
        ( A ) NAME/KEY: Other
        ( B ) LOCATION: 1...1
        ( D ) OTHER INFORMATION: Position 1 corresponds to
            8137 of the rabbit cDNA homolog ( x i ) SEQUENCE DESCRIPTION: SEQ ID NO:5:

```
ATAATTCCTG AGAAGTTGGA ATACTTCATT                                      30
```

( 2 ) INFORMATION FOR SEQ ID NO:6:

( i ) SEQUENCE CHARACTERISTICS:
        ( A ) LENGTH: 900 base pairs
        ( B ) TYPE: nucleic acid
        ( C ) STRANDEDNESS: both
        ( D ) TOPOLOGY: linear ( i i ) MOLECULE TYPE: Genomic DNA ( i i i ) HYPOTHETICAL: NO ( i v ) ANTI-SENSE: NO ( v ) FRAGMENT TYPE:

( v i ) ORIGINAL SOURCE:

( i x ) FEATURE:
        ( A ) NAME/KEY: Other
        ( B ) LOCATION: 1...1
        ( D ) OTHER INFORMATION: Position 1 corresponds to
            8137 of the rabbit cDNA homolog
        ( A ) NAME/KEY: Other
        ( B ) LOCATION: 230...230

(D) OTHER INFORMATION: Position distinguishes idiopathic
  dilated cardiomyopathy
(A) NAME/KEY: Other
(B) LOCATION: 626...626
(D) OTHER INFORMATION: Position distinguishes idiopathic
  dilated cardiomyopathy (xi) SEQUENCE DESCRIPTION: SEQ ID NO:6:

```
ATAATTCCTG AGAAGTTGGA ATACTTCATT AACAAATATG CAGAACATTC TCATGACAAA      60
TGGTCAATGG ACAAGTTAGC AAATGGATGG ATTTATGGAG AAATATATTC AGACTCCTCC     120
AAGATTCAAC CCTTGATGAA ACCATATAAA CTATTATCTG AAAAGGAAAA AGAAATTTAT     180
CGCTGGCCAA TCAAAGAATC TCTCAAAACT ATGTTGGCTT GGGGTTGGAA GATTGAAAGA     240
ACCCCAGAAG GAGACAGCAT GGCCCTTTAT AACCGAACTC GTCGTATTTC TCAGACAAGC     300
CAGGTTTCTG TAGATGCTGC CCATGGTTAT AGTCCCCGAG CCATTGACAT GAGCAATGTT     360
ACACTATCCA GAGACCTGCA TGCTATGGCA GAAATGATGG CTGAAAACTA TCATAACATA     420
TGGGCAAAGA AAAAGAAACT GGAGTTGGAG TCTAAAGGAG GTGGAAACCA TCCTCTGCTG     480
GTACCCTATG ATACGCTGAC AGCCAAAGAG AAAGCCAAGG ATAGGGAAAA GGCACAGGAC     540
ATCCTCAAGT TCTTGCAGAT CAATGGATAT GCTGTATCCA GAGGATTCAA GGACCTGGAA     600
CTGGACACAC CTTCCATTGA GAAGCTTTTC GCCTATAGTT TCCTCCAGCA ACTTATCCGC     660
TATGTGGATG AAGCTCATCA GTACATCCTG GAGTTTGATG GTGGCAGCAG AAGCAAAGGA     720
GAACATTTCC CTTATGAACA AGAAATCAAG TTCTTTGCAA AAGTCGTTCT ACCTTTAATT     780
GATCAGTATT TCAAAAACCA TCGTTTATAC TTCTTATCTG CAGCAAGCAG ACCTCTCTGC     840
TCTGGAGGGC ATGCATCAAA CAAAGAGAAG GAAATGGTGA CTAGCCTATT CTGCAAACTT     900
```

GENE MUTATION IN PATIENTS WITH IDIOPATHIC DILATED CARDIOMYOPATHY

GOVERNMENT INTEREST IN THE INVENTION

Certain aspects of the invention disclosed herein were made with United States government support under NIH-Heart, Lung & Blood Institute grant HL48509. The United States government has certain rights in these aspects of the invention.

FIELD OF THE INVENTION

The present invention relates generally to the field of genetic screening for inherited disease. More specifically, the invention regards a method of identifying individuals at risk of developing idiopathic dilated cardiomyopathy.

BACKGROUND OF THE INVENTION

Idiopathic dilated cardiomyopathy, formerly called congestive cardiomyopathy, is a syndrome characterized by cardiac enlargement and congestive heart failure. Although no etiology is definable in most cases, the congestive cardiomyopathy is believed to represent the result of myocardial damage caused by toxic, metabolic or infectious agents. Diagnosis of this disease depends solely on the exclusion of other possible causes at a late stage of the disorder. Nearly 40% of the patients receiving heart transplants suffer from idiopathic dilated cardiomyopathy.

Abnormal modulation of intracellular calcium has been proposed as the key mechanism underlying the systolic and diastolic dysfunctions that accompany heart failure associated with cardiomyopathy. Recently, several studies have documented the pathogenetic role of abnormal sarcoplasmic reticulum (SR) function in various cardiomyopathies. For example, $Ca^{++}$-ATPase expression is decreased in patients having end-stage heart failure caused by the various cardiomyopathies.

The relationship between systolic function and intracellular calcium is not consistent among the different animal models that have been used to study cardiomyopathies. However, an excellent correlation has been demonstrated between systolic dysfunction and decreased availability of activation calcium in Syrian hamsters having end-stage dilated cardiomyopathy. The mechanism underlying abnormal intracellular calcium regulation in cardiomyopathies has not been explained previously.

SUMMARY OF THE INVENTION

One aspect of the present invention is an isolated polynucleotide encoding a mutant human SR $Ca^{++}$ release channel. This polynucleotide comprises the sequence of SEQ ID NO:3 with the exception of having nucleotide positions 380 and 776 substituted by residues other than guanosine. Nucleotide position 380 can be substituted by adenosine, and/or nucleotide position 776 substituted by thymidine.

Another aspect of the invention is a method of identifying an individual genetically predisposed to idiopathic dilated cardiomyopathy. This method includes the steps of: obtaining a tissue sample from the individual, obtaining a population of polynucleotides from the tissue sample, determining if the population includes a polynucleotide having the sequence of SEQ ID NO:3 except with a substitution at either position 380 or 776. The individual is identified as being genetically predisposed to idiopathic dilated cardiomyopathy if the polynucleotide is present. The tissue sample can be any of a number of types of samples, such as a sample of blood or a sample of cardiac myocytes. The determining step comprises PCR amplification and/or DNA sequencing. In certain cases, a substitution of adenosine at position 380 of SEQ ID NO:3 or a substitution of thymidine at position 776 of SEQ ID NO:3 is identified. In one embodiment, the determining step comprises cleavage by a restriction endonuclease, such as HindIII followed by electrophoresis. In this embodiment, cleavage can sometimes result in the formation of two polynucleotide fragments, such as fragments having lengths of from between about 300 and 800 base pairs. In a preferred embodiment, the determining step comprises identifying a 3.7 kb HindIII restriction fragment length polymorphism, wherein the presence of the fragment indicates the presence of the polynucleotide.

A further aspect of the present invention is a pair of oligonucleotides primers for amplifying a segment of the SR $Ca^{++}$ release channel gene. A first of the pair is homologous to a sequence contained within SEQ ID NO:4 on one side of a region including a HindIII restriction endonuclease cleavage site at position 777 of the sequence of SEQ ID NO:4, and a second of the pair is homologous to a sequence contained within SEQ ID NO:4 on another side of the region. The pair of primers can have the sequences SEQ ID NO:1 and SEQ ID NO:2 or SEQ ID NO:5 and SEQ ID NO:2.

Yet another aspect of the invention is an immunohistochemical method of identifying an individual at risk of idiopathic dilated cardiomyopathy. This method includes the step of obtaining first and second antibody reagents. The first antibody has binding specificity for a wild-type SR $Ca^{++}$ release channel, and the second antibody has binding specificity for a mutant SR $Ca^{++}$ release channel. The mutant SR $Ca^{++}$ release channel is expressed in individuals afflicted with idiopathic dilated cardiomyopathy. The method also includes the steps of obtaining from the individual a tissue sample containing cardiac myocytes, testing the myocytes for staining by the first and second antibody reagents, and identifying individuals at risk of idiopathic dilated cardiomyopathy as those individuals whose myocytes were stained by the second antibody but not by the first antibody.

Still another aspect of the present invention is a lipid bilayer having incorporated therein a substantially purified mutant SR $Ca^{++}$ release channel protein obtained from a mammal genetically predisposed to idiopathic dilated cardiomyopathy. The substantially purified mutant SR $Ca^{++}$ release channel protein can be derived from sarcoplasmic reticulum membranes isolated from myocardium membranes.

One more aspect of the invention is a method of identifying drugs useful in the treatment of individuals afflicted with idiopathic dilated cardiomyopathy. This method includes the steps of (a) preparing a first lipid bilayer having incorporated therein SR $Ca^{++}$ release channels substantially purified from cardiac myocytes obtained from an individual afflicted with idiopathic dilated cardiomyopathy and (b) preparing a second lipid bilayer having incorporated therein SR $Ca^{++}$ release channels substantially purified from cardiac myocytes obtained from an individual not afflicted with idiopathic dilated cardiomyopathy. An assay is performed to measure SR $Ca^{++}$ release channel gating properties of the first and second bilayers in the absence and presence of a test drug. The results of the assay in the absence and presence of the test drug are compared. Drugs are identified as useful in treating individuals afflicted with idiopathic dilated cardiomyopathy as a test drug which causes causing mutant SR $Ca^{++}$ release channels of step (a) to exhibit gating properties similar to those of wild type SR $Ca^{++}$ release channels of step (b). Gating properties that can be measured include single channel open probability, open and close lifetimes and single channel current voltage.

DETAILED DESCRIPTION OF THE INVENTION

Figure 1A:
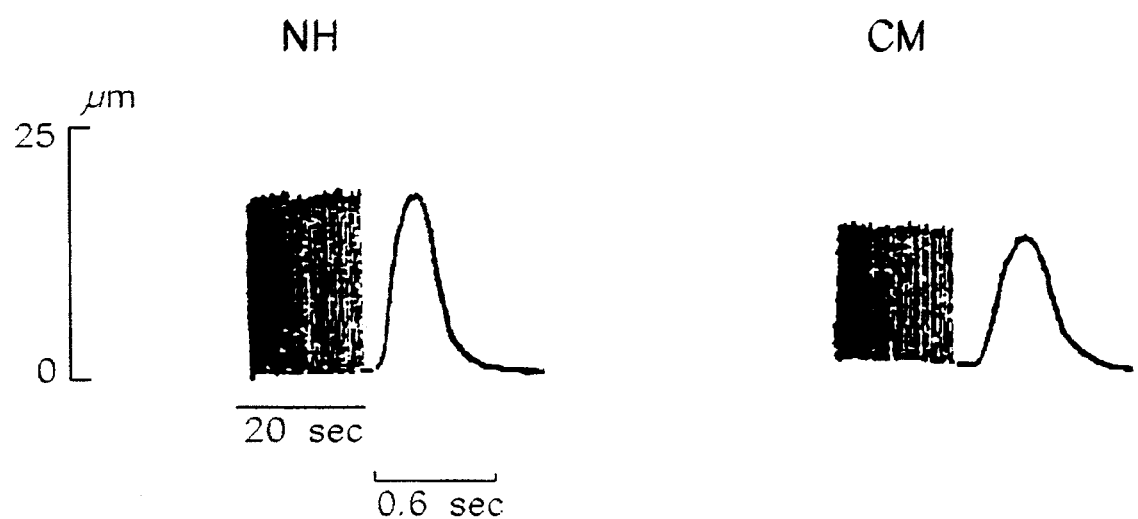
FIGS. 1A and 1B show the contractile amplitude of isolated cardiac myocytes from the cardiomyopathic hamster hearts at prehypertrophic, hypertrophic and heart failure stages and age-matched normal hamster hearts. (A) Superimposed are the amplitude of cell motion traces recorded from a hypertrophic myocyte (CM) and an age-matched normal myocyte (NH). The resting cell length for CM was 178 µm and NH was 154 µm. (B) Means and S.D. for the amplitude of cell motions normalized by resting maximal cells length in normal (open bars) (n=20 for each age group) and cardiomyopathic (hatched bars) (n=20 for each age group) were shown in 0.9 mM $[Ca]_o$.

We have discovered that the presence of a mutation within the SR $Ca^{++}$ release channel gene is indicative of susceptibility to idiopathic dilated cardiomyopathy. Based on this discovery, we have created a genetic screening test that can identify individuals who have, or who are susceptible to, idiopathic dilated cardiomyopathy. The invented screening test provides the only known method of diagnosing idiopathic dilated cardiomyopathy or susceptibility to this disease.

As disclosed below, a mutation within the gene which encodes the $Ca^{++}$ release channel (also known as the ryanodine receptor) correlated with the disorder known as idiopathic dilated cardiomyopathy. Individuals identified by the invented methods as being at risk for this disease can be advised to avoid exposure to other risk factors associated with this disease. Such risk factors include alcohol, exposure to toxins and diabetes. Thus, knowledge that an individual is susceptible to idiopathic dilated cardiomyopathy advantageously provides a means for preventing or delaying disease onset.

Further, diagnosis of idiopathic dilated cardiomyopathy at an early stage following disease onset allows for more specific treatment of the disease. Rather than providing a general treatment of the disease symptoms until the time of heart failure, progress of the disease could be slowed. The patient's lifespan will certainly be extended as the result of an early diagnosis and intervention. However, until now no test was available for making such an early diagnosis.

An important point regards the nomenclature used herein when referring to the numbering of the nucleotides representing the human SR $Ca^{++}$ release channel gene sequence. The 16 kb cDNA sequence encoding the rabbit SR $Ca^{++}$ release channel has been published by Otsu et al., in *J. Biol Chem.* 265:13472 (1990). The nucleotide sequence of the human homolog has not been published and is not on deposit in a publicly accessible data base. However, we and others have determined that the polynucleotide sequences representing the human and rabbit SR $Ca^{++}$ release channel genes are highly similar. Thus, for convenience, we refer to the newly discovered mutations in the human polynucleotide sequence in terms of the numbering of the published rabbit cDNA sequence. Thus, the point mutations at positions 380 and 776 of the cloned sequence presented as SEQ ID NO:4 correspond to positions 8366 and 8762 of the cDNA sequence disclosed by Otsu et al.

The initial discoveries that led to the development of the invention were made using cardiac myocytes isolated from the Bio 14.6 strain of hamster that is genetically predisposed to develop idiopathic dilated cardiomyopathy. Abnormal $Ca^{++}$ homeostasis is believed to contribute to the development of cardiac hypertrophy and heart failure in these laboratory animals. The following experiments were performed to explore possible irregularities in calcium sequestration or calcium release from intracellular stores in the sarcoplasmic reticulum (SR).

Although other materials and methods similar or equivalent to those described herein can be used in the practice or testing of the present invention, the preferred methods and materials are now described. General references for methods that can be used to perform the various PCR and cloning procedures described herein can be found in *Molecular Cloning: A Laboratory Manual* (Sambrook et al. eds. Cold Spring Harbor Lab Publ. 1989) and *Current Protocols in Molecular Biology* (Ausubel et al. eds., Greene Publishing Associates and Wiley-Interscience 1987). The disclosures of these references are hereby incorporated by reference.

Example 1 describes the method used to isolate the ventricular myocytes that were used to study calcium handling. Myocytes were prepared from cardiomyopathic hamsters at prehypertrophic, hypertrophic, and heart failure stages.

EXAMPLE 1

Isolation of Ventricular Myocytes from Cardiomyopathic Hamsters

Male Bio 14.6 cardiomyopathic and FIB healthy control hamsters were obtained from Biobreeders (Fitchburg, Mass.). The animals were obtained at developmental stages representing the prehypertrophic (20–30 days old), hypertrophic (130–170 days old) and heart failure stages (440–480 days old). Both cardiomyopathic and the healthy control hamsters were maintained under the same conditions on a normal laboratory animal diet and tap water ad libitum.

Normal and cardiomyopathic hamsters were anesthetized with ether. The hearts were rapidly removed and perfused via a cannula in the aorta with oxygenated warm (37° C.) Krebs-Henseleit bicarbonate buffered solution (pH 7.30) containing (mM) NaCl 118; KCl 4.7; $CaCl_2$ 0.6; $MgSO_4$ 1.20; $KH_2PO_4$ 1.20; $NaHCO_2$ 25 and dextrose 15. During this perfusion, regular contractions occurred as the heart was cleared of blood. After 8 minutes (6 ml/minute), perfusion was continued with $Ca^{++}$-free Krebs-Henseleit buffer. The heart ceased to contract following transition to this medium. Subsequently, 0.05% collagenase and 0.03% hyaluronidase were added to the $Ca^{++}$-free medium which was recirculated through the heart. Perfusion was continued for 30 minutes as the heart became enlarged. The ventricle was removed from the perfusion set-up, cut into 2 $mm^3$ pieces and placed in a flask containing 0.05% collagenase, 0.03% hyaluronidase, 0.001% trypsin and 1.0 mM $CaCl_2$ in Krebs-Henseleit buffer. The tissue fragments were shaken (100 cycles/minute) in an orbital shaking water bath at 37° C. After 15 minutes, the tissue pieces were transferred into a $Ca^{++}$-free buffer containing 0.05% collagenase and 0.03% hyaluronidase. The tissue pieces were triturated 5 minutes using a 5 ml plastic pipette with a 6 mm orifice. Warm (37° C.) oxygenated $Ca^{++}$-free buffer was added to the tube, and the cells were centrifuged at 400 rpm (41×g) for 1 minute. The pelleted cells were then washed twice, using the same method, to remove the collagenase and hyaluronidase enzymes. Isolated myocytes were resuspended in 0.6 mM $Ca^{++}$ solution. Approximately 80% of cells exhibited rod-shaped morphology with clear cross-striations.

Cells isolated according to the method described above were used to assess the contractile properties of myocytes obtained from hearts representing the various stages of disease progression. More specifically, the amplitudes of cell motion were measured in ventricular myocytes isolated from cardiomyopathic hamsters at the prehypertrophic stage (20–30 days old), hypertrophic (130–170 days old) or heart failure stage (440–480 days old) of development. As detailed below, comparisons were made with age and sex-matched normal controls (FIB).

Example 2 describes the methods used to quantitate the contractile properties of ventricular myocytes.

EXAMPLE 2

Measurement of Myocyte Contractility

Isolated adult cardiac myocytes were attached to glass coverslips with collagen (Vitrogen 400) and placed in a chamber that allowed for continuous flow of perfusion medium over the monolayer. The chamber was placed on the stage of an inverted phase-contrast microscope (Lietz-Diavert, The Lietz Co., Overland Park, Kans.) enclosed in a Lucite box and maintained at 37° C. The cells were perfused at a rate of 1 ml/minute with a physiological solution containing (mM) HEPES 5, $CaCl_2$ 0.9, KCl 4.0, NaCl 140, $MgCl_2$ 0.5, and glucose 11 (pH 7.35). The cells were electrically stimulated at a frequency of 1.5 Hz using a platinum electrode. The cells were magnified using a 40× objective. A single cell image was monitored by a low light level silicon TV camera attached to the microscope observation tube with a 2× coupler. The TV camera video output was connected to a video motion detector and displayed on a Panasonic TV monitor. The total magnification of the image on the monitor screen was 2000×. The TV camera had an interlace defeat producing an image composed of 262 raster lines. The motion detector monitored a selected raster-line segment and provided the amplitude of cell moving along the raster line at a sampling interval of 16 ms. Light-dark contrast at the edge of the cell provided a marker for measurement of the amplitude of motion. The analog tracing was recorded with a strip charge recorder. Cells chosen from experiments always contracted from an attachment point at the center of the cell. Both freely moving ends of the cell shortened with stimulation and the amplitude of the cell motion was same at both ends.

Figure 1B:
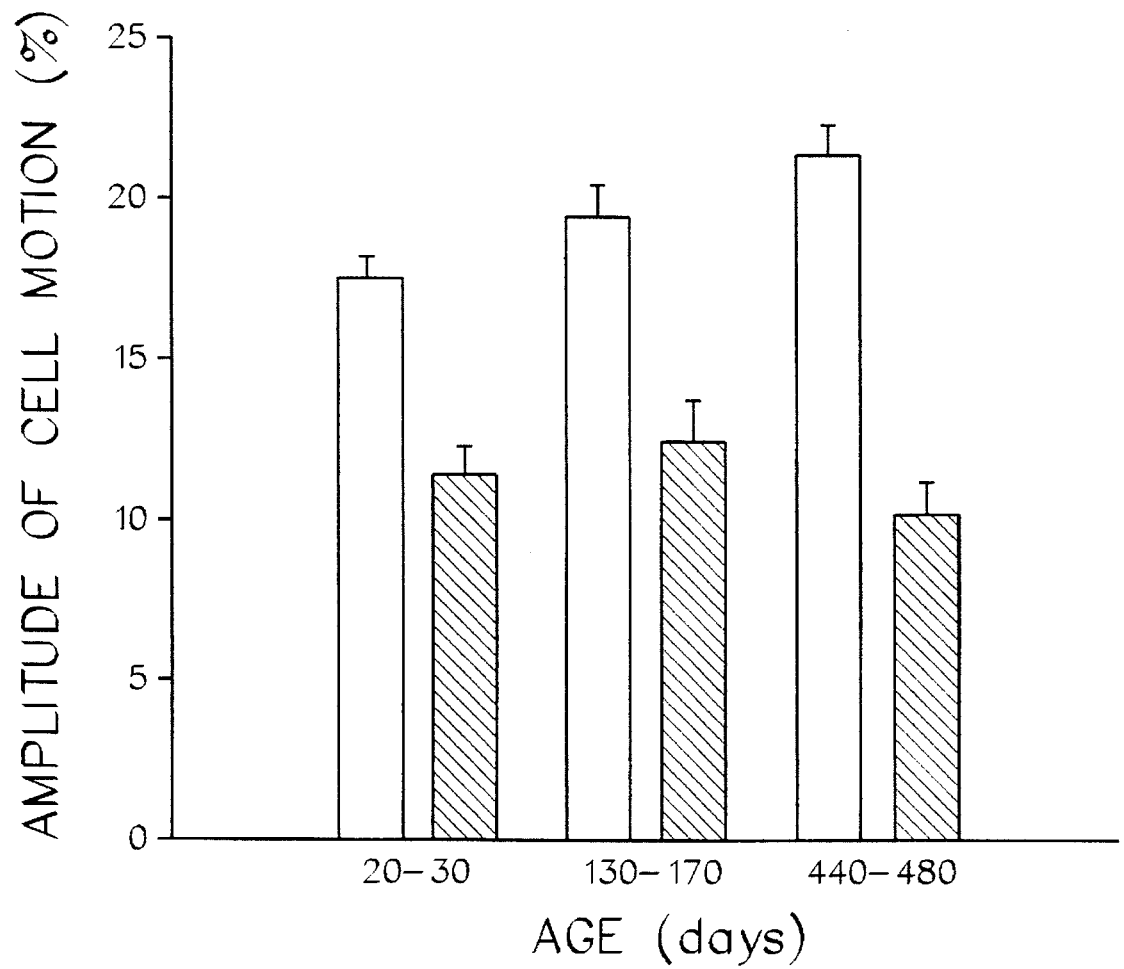

Results of these procedures indicated that the resting maximum cell length was slightly longer in prehypertrophic hearts (67±16 μm, n=60) than in age-matched normal controls (59±10 μm, n=60). However, this difference was not statistically significant (p=0.06). In cells representing hypertrophic and heart failure stages, the resting cell length was significantly greater (179±28 μm and 186±22 μm, respectively, n=60) than normal controls (154±18 μm and 165±19 μm, respectively, n=60, p<0.05). Therefore, the amplitude of cell motion recorded from both cell ends was normalized to the resting cell length. As shown in FIG. 1, the amplitude of cell motion in isolated myocytes from cardiomyopathic hamsters at the prehypertrophic stage was 11.4±0.9% (n=20). These values were significantly lower than those obtained using myocytes from age-matched normal controls (17.4±0.7%, n=20, p<0.05). The amplitude of cell motion increased in normal cells with age, from 19.2±1.0% at 130–170 days, to 20.9±0.9% at 440–480 days (p<0.05, n=20). The amplitude of contraction of hypertrophic myocytes (12.3±1.2%, n=20) was greater than that measured for prehypertrophic cells (p<0.05), but was significantly less than that measured for age-matched normal controls (p<0.05). Cells isolated from hamsters that exhibited heart failure gave amplitudes of cell motion that were significantly lower (10.0±1.1%, n=20) than those recorded for age-matched controls (n=20, p<0.01).

The results presented in the preceding Example indicated quantitative differences between the amplitudes of myocyte contractility for cells isolated from Bio 14.6 and normal control hamsters. The cause of these differences remained to be determined. The starting point for studies aimed at making this determination involved an examination of the $^{45}Ca^{++}$ uptake for cardiac myocytes isolated from three developmental stages of the myopathic and age-matched normal hamsters.

Example 3 describes the methods used to assess calcium flux in myocytes derived from cardiomyopathic and control hamster hearts.

EXAMPLE 3

Analysis of Calcium Flux in Myocytes

The procedure for measuring the $^{45}Ca^{++}$ uptake rate was essentially that described by Barry et al., in *J. Physiol*

325:243 (1982). Isolated cells were prepared simultaneously from cardiomyopathic and control hamster hearts, suspended in 2 ml of Krebs-Hanseleit buffer with 20% albumin and allowed to settle for 5 minutes through the albumin at 37° C. The supernatant was then removed, and the sedimented viable cells were resuspended in 37° C. HEPES-buffered media containing 0.9 mM $Ca^{++}$. Cells from either preparation were about 95% rod shaped. Cells were then incubated for periods of from 15 seconds to 60 minutes at 37° C. in a 0.5 ml volume of medium containing $^{45}Ca^{++}$ (5 μCi/ml). Cells were filtered by suction and washed three times with 4 ml of ice-cold HEPES containing no radiolabeled ions. Filters were dried and counted in an LKB 1219 RackBata liquid scintillation counter (Gaithersburg, Md.). Protein content was measured by standard methods using bovine serum albumin as a standard.

Figure 2:
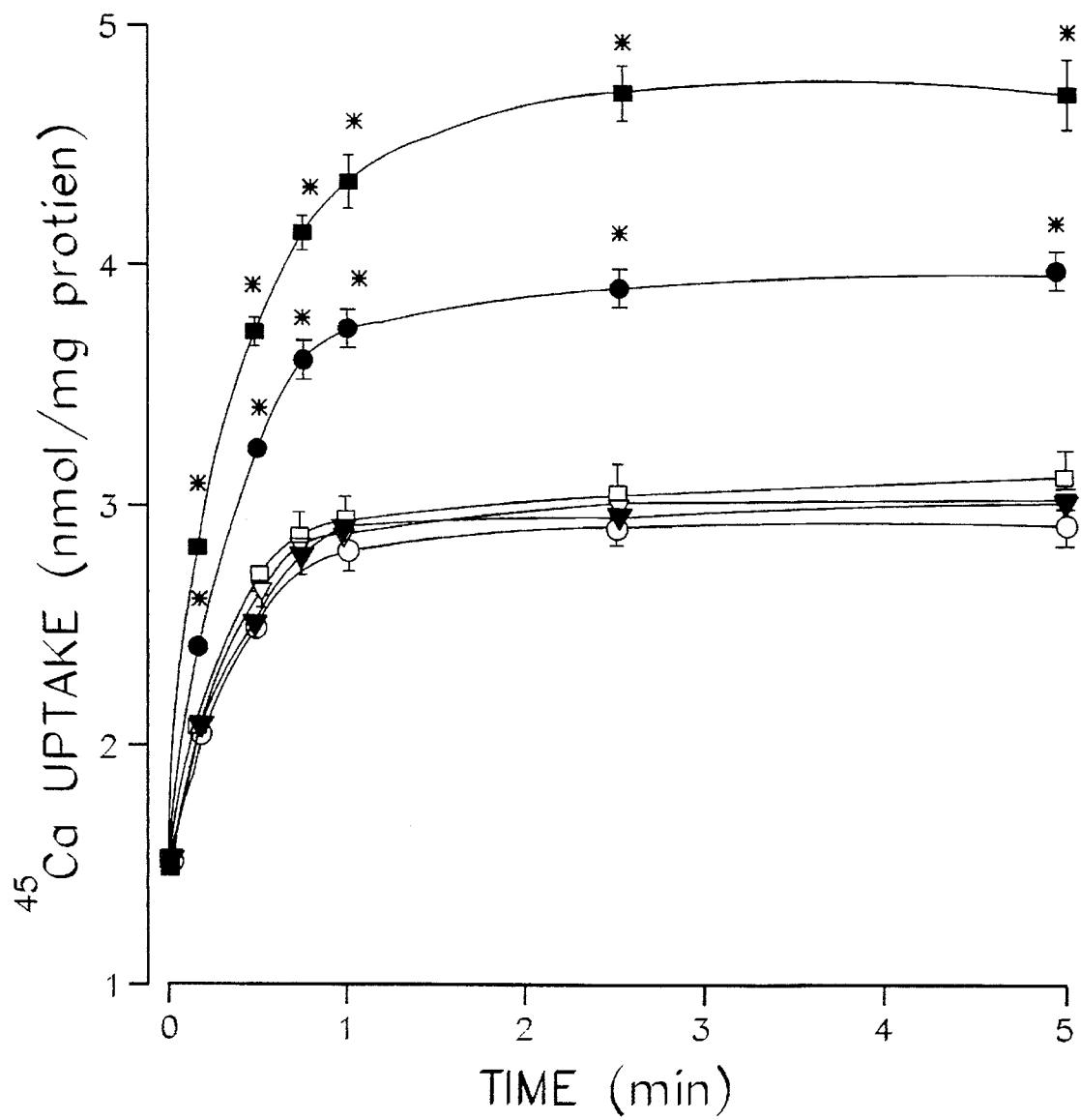
FIG. 2 shows $^{45}Ca^{++}$ uptake by cardiac myocytes isolated from cardiomyopathic hamster hearts at three developmental stages and age-matched normal hearts. Values shown are mean±S.D. for cardiomyopathic cells (filled symbols) at prehypertrophic (triangles), hypertrophic (circles) and hearts failure (squares) stages and age-matched normal cells (filled symbols). Each point is the mean of data from 10 experiments performed in triplicate. * $p<0.01$.

Results of this procedure are presented in FIG. 2. As indicated, $^{45}Ca^{++}$ uptake was similar in prehypertrophic cells and in age-matched normal control cells. In the normal cells, the rate of $^{45}Ca^{++}$ uptake was unchanged with age. However, the uptake of $^{45}Ca^{++}$ proceeded more rapidly in myopathic cells at the hypertrophic stage (26±4%) than in normal controls (n=10, p<0.01). The $^{45}Ca^{++}$ content remained consistently 35±4% higher than control cells at 5 minute plateaus. Furthermore, the initial rate of $^{45}Ca^{++}$ uptake, as well as the size of the rapidly exchangeable calcium pool, were increased 50%±6% in the cells isolated from the cardiomyopathic hamster hearts at the heart failure stage when compared with age-matched control cells (n=10, p<0.01).

To obtain further insight into intracellular free $Ca^{++}$ ($[Ca^{++}]_i$) handling and its relation to contractile behavior, transient $[Ca^{++}]_i$ was measured in three stages of myopathic myocytes and age-matched normal control cells.

Example 4 describes the methods used to measure intracellular $Ca^{++}$ concentrations.

EXAMPLE 4

Measurement of Intracellular $Ca^{++}$ Concentration $[Ca^{++}]_i$ of single cardiac myocytes obtained from cardiomyopathic and control hamsters were measured using the $Ca^{++}$-sensitive fluorescent dye, fura-2. Cells attached to glass coverslips were incubated with 3 μM fura-2 AM for 10 minutes at room temperature and then washed for 5 minutes in HEPES-buffered medium to remove extracellular and bound dye. The glass coverslip with attached cells was placed in a perfusion chamber specifically designed to fit the stage of a phase-contrast microscope (Nikon Inc., Garden City, N.Y.) and perfused with oxygenated HEPES-buffered medium warmed to 37° C. The microscope with a 40× objective was attached to a SPEX-fluorolog 2 instrument with excitation wavelengths set at 340 nm and 380 nm and emission wavelength set at 505 nm. The two excitation wavelengths were made to alternate once every second for time-averaged $[Ca^{++}]_i$ measurements or 100 times per second for transient $[Ca^{++}]_i$ measurements and were stored in separate memories of an SPEX Datamate microcomputer (SPEX Industries, Inc., Edison, N.J.).

Cells chosen for $[Ca^{++}]_i$ measurement were electrically stimulated at 1.5 Hz using platinum electrodes. Contractions that followed stimulation were visually confirmed before, during, and after each experiment. After equilibration, the fluorescence signal was continuously monitored. At the end of each experiment, background autofluorescence from cells not loaded with fura-2 was subtracted from the original signals. In most cases the background signal was less than 1% of the fluorescence signal from the fura-2 loaded cell. In order to calibrate the signals to represent actual $[Ca^{++}]$ values the cells were perfused with a HEPES-buffered medium containing ionomycin (3 μM) and digitonin (20 μg/ml) to obtain the maximum fluorescence. Cells were then perfused with $Ca^{++}$-free medium containing 5 mM EGTA to obtain the minimum fluorescence signal. The equation disclosed by Grynkiewicz, et al., in *J. Biol. Chem.* 260:3440 (1985) was used to transform the 340/380 nm fluorescence intensity ratios into $[Ca^{++}]_i$ values. Notably, use of the ratio (340/380 nm) compensated for variations involving dye concentration, dye leakage and cell thickness. Under the conditions of our studies, 3 μM fura-2 exposure for 10 minutes reduced the amplitude of cell motion by approximately 115%. Washing the cells produced no further decline in cell motion. Any cell in which fura-2 decreased the amplitude of cell motion by more than 30% was not used.

Figure 3:
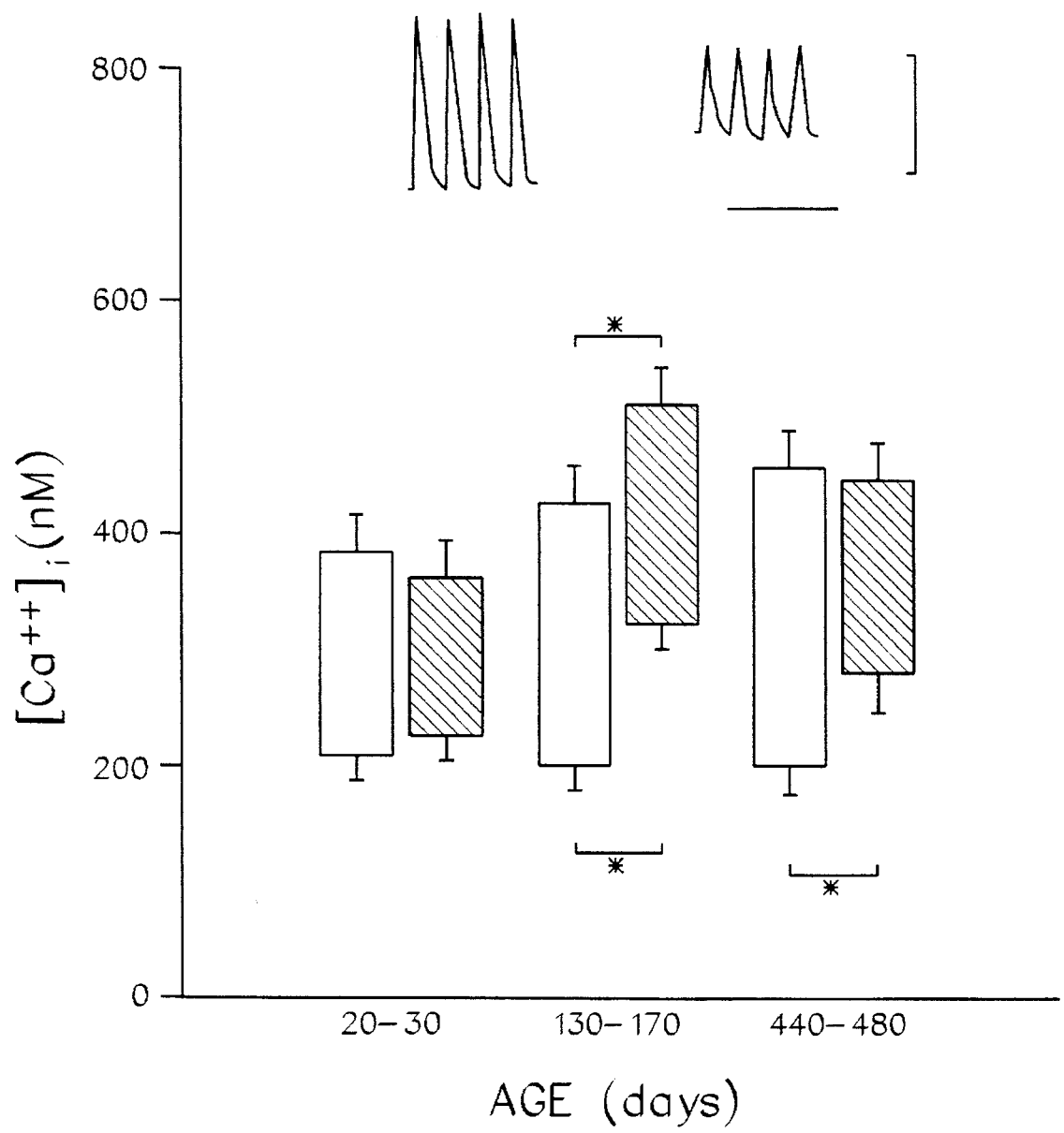
FIG. 3 shows $[Ca^{++}]_i$ transient in cardiac myocytes from cardiomyopathic hamster hearts at three developmental stages and age-matched hamster hearts. $[Ca^{++}]_i$ transient associated with single contraction was examined using fura-2 fluorescence. Cells were electrically driven at 1.5 Hz using platinum electrodes. Superimposed are the $[Ca^{++}]_i$ transients recorded from a cardiomyopathic cell (CM) at heart failure stage and an age-matched normal cell (NH). Values shown are mean±S.D. for 18 cells from cardiomyopathic hamster hearts (hatched bars) at each age-groups and 18 cells from age-matched normal hamster hearts (open bars). * $p<0.01$.

Results of these procedures are presented in FIG. 3. The amplitude of $[Ca^{++}]_i$ transient increased with age in normal myocytes. The systolic $[Ca^{++}]_i$ in prehypertrophic cells (362±32 nM, n=18) was slightly lower than that in age-matched normal cells (384±31 nM, n=18, p=0.06). The diastolic $[Ca^{++}]_i$ was slightly higher in myopathic cells at the prehypertrophic stage (224±23 nM, n=18) than in age-matched normal cells (208±23 nM; n=18, p=0.06). Although the differences in both systolic and diastolic $[Ca^{++}]_i$ between the two groups was not statistically significant, the amplitude of the change in $[Ca^{++}]_i$ transient was significantly reduced in myopathic cells at the prehypertrophic stage (p<0.01). In the hypertrophic cells systolic and diastolic $[Ca^{++}]_i$ values were elevated to 543±31 nM and 317±23 nM, respectively. The amplitude of the $[Ca^{++}]_i$ transient was significantly lower than that in age-matched normal cells (p<0.01). The percentage of decrease in the amplitude of the $[Ca^{++}]_i$ transient in hypertrophic cells (17±4%) was similar as that in prehypertrophic cells (21±3%) compared with that in age-matched normal cells. In myopathic cells at the heart failure stage, diastolic $[Ca^{++}]_i$ was lower (272±31 nM) than that in hypertrophic cells, but was significantly higher than that in age-matched control cells (193±24 nM, n=18, p<0.001). Systolic $[Ca^{++}]_i$ value (437±30 nM) was greatly reduced compared to that in hypertrophic cells, but was not significantly different than that measured in age-matched normal cells (448±30 nM, n=18, p. 0.07). The amplitude of $[Ca^{++}]_i$ transient was greatly reduced compared to that in hypertrophic or age-matched control cells (p<0.001).

These results indicated that the $[Ca^{++}]_i$ transients of the two groups at the prehypertrophic stage were not substantially different. In hypertrophic myocytes, however, there was an increase in both systolic and diastolic $[Ca^{++}]_i$ when compared with age-matched control cells. Since the increment of the systolic $[Ca^{++}]_i$ was more than the diastolic $[Ca^{++}]_i$, the difference between systolic and diastolic $[Ca^{++}]_i$ was also significantly increased in hypertrophic cells when compared with age-matched control cells. The delayed appearance of an enhancement of end-diastolic $[Ca^{++}]_i$ in hypertrophic cells implicated the alteration in SR $Ca^{++}$ reuptake or $Ca^{++}$ exclusion through the sarcolemma in myopathic cells. The delayed appearance of elevated cytosolic $Ca^{++}$ may be secondary to another defect in this genetically determined cardiomyopathy.

The next step in the development of the invention involved testing the possibility that release of intracellular $Ca^{++}$ could be stimulated by means other than electrical excitation. Caffeine treatment, which is known to stimulate $Ca^{++}$ release by SR $Ca^{++}$ release channels, was employed in these experiments.

Example 5 describes the methods used to examine the effect of caffeine on SR channel function in 130–170 day old normal and cardiomyopathic hamster myocytes.

EXAMPLE 5

Inotropic Response to Caffeine

Cardiac myocytes isolated from hypertrophic and age-matched normal hamsters, prepared as in Example 1, were perfused with $Na^+$-free HEPES buffer for 5 minutes, and then exposed to 20 mM caffeine in $Na^+$- and $Ca^{++}$-free HEPES buffer to assess SR $Ca^{++}$ content without the presence of $Na^+$-$Ca^{++}$ exchange.

Figure 4:
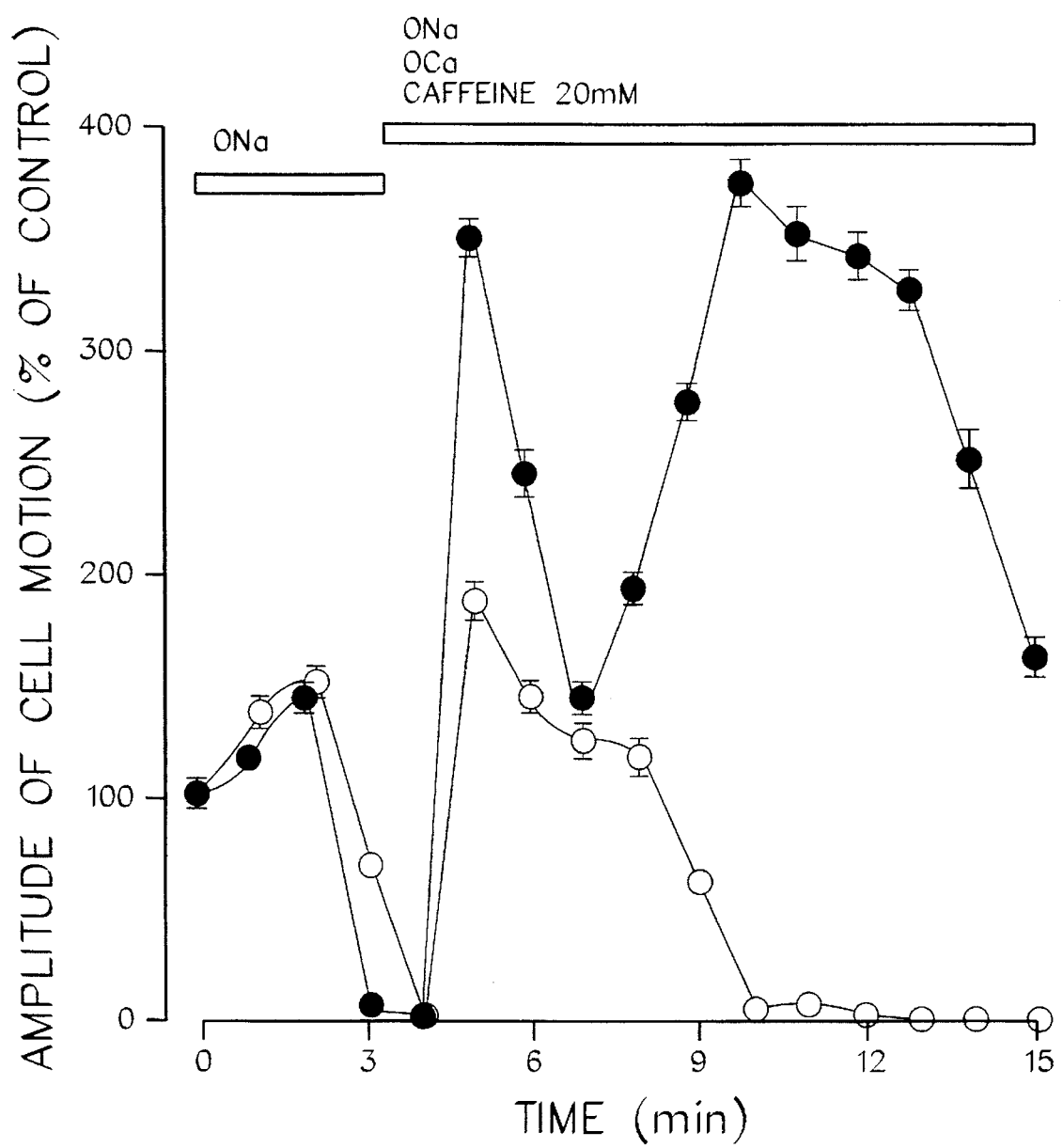
FIG. 4 shows the contractile response to caffeine. Isolated ventricular myocytes from 130–170 days old normal (open circles) and cardiomyopathic (filled circles) hamsters were electrically stimulated at 1.5 Hz while superfused with HEPES-buffered medium (pH 7.35, 37° C.) containing 0.9 mM $Ca^{++}$. After equilibration, cells were perfused with Na+- and $Ca^{++}$-free HEPES buffer to assess SR $Ca^{++}$ stores. Data are plotted as a percentage change of the contractile amplitude from control condition. Each point represents the mean±S.D. of 16 experiments using cells from 6 normal and 6 myopathic hearts.

FIG. 4 shows the response to caffeine expressed as a percentage of change in amplitude of cell motion from baseline ($[Ca^{++}]_o$=0.9 mM). The time-course of the effect of the $Na^+$-free buffer alone (0–4 minutes) was similar in myopathic and normal cells. The amplitude of cell motion was increased 48% in myopathic cells and 56% in normal cells as compared to those under control conditions (n=16, p>0.05). After cells were perfused with $Na^+$- and $Ca^{++}$-free medium containing caffeine, the amplitude of cell motion was increased 3.49 fold in the myopathic cells was compared with control cells. This increment was significantly greater than that in normal cells (1.87 fold, n=16, p<0.05). Although the cell motion at the control condition was 48% lower in myopathic cells than in the normal cells, maximal amplitude of cell motion induced by caffeine reached the same level in myopathic cells as in normal cells (p> 0.05). The effect of 20 mM caffeine with a zero $Na^+$ and $Ca^{++}$ superfusion on cell contraction was more prolonged in myopathic cells (11±2 minutes) than in normal cells (6±1 minute, p<0.05). A complex multiphasic pattern was also evident.

The striking difference between the effects of caffeine on $Ca^{++}$ release in normal and cardiomyopathic myocytes suggested that some feature of the SR $Ca^{++}$ release channel distinguished the normal and disease-prone animals.

The following Example discloses experimental results that confirmed a significantly abnormal $Ca^{++}$ release channel function in the animal model for cardiomyopathy. Most importantly, this abnormality was detectable at a prehypertrophic stage of the disease. This vital finding suggested that a diagnostic test for the genetic disease could be based on some feature which distinguished the normal and disease-prone $Ca^{++}$ release channel genes or gene products.

Example 6 describes the methods used to compare the SR $Ca^{++}$ release channel functions in Bio 14.6 hamsters at the prehypertrophic stage, at the heart failure stage and in age-matched normal controls.

EXAMPLE 6

Abnormality in SR $Ca^{++}$ Release at Prehypertrophic Stage

SR vesicles were prepared from cardiomyopathic and normal hamster hearts at ages 30 to 40 days and 200 to 300 days according to the method described by Meissner et al., in *J. Biol. Chem.* 262:3065 (1987). Homogenates were initially subjected to differential centrifugation. The subfraction of cardiac SR vesicles was then isolated using a sucrose step density gradient. The free $Ca^{++}$ activity inside SR vesicles was determined by measurement of the fluorescence ratio (340/380 nm) in fura-2-loaded SR vesicles.

Figure 5A:
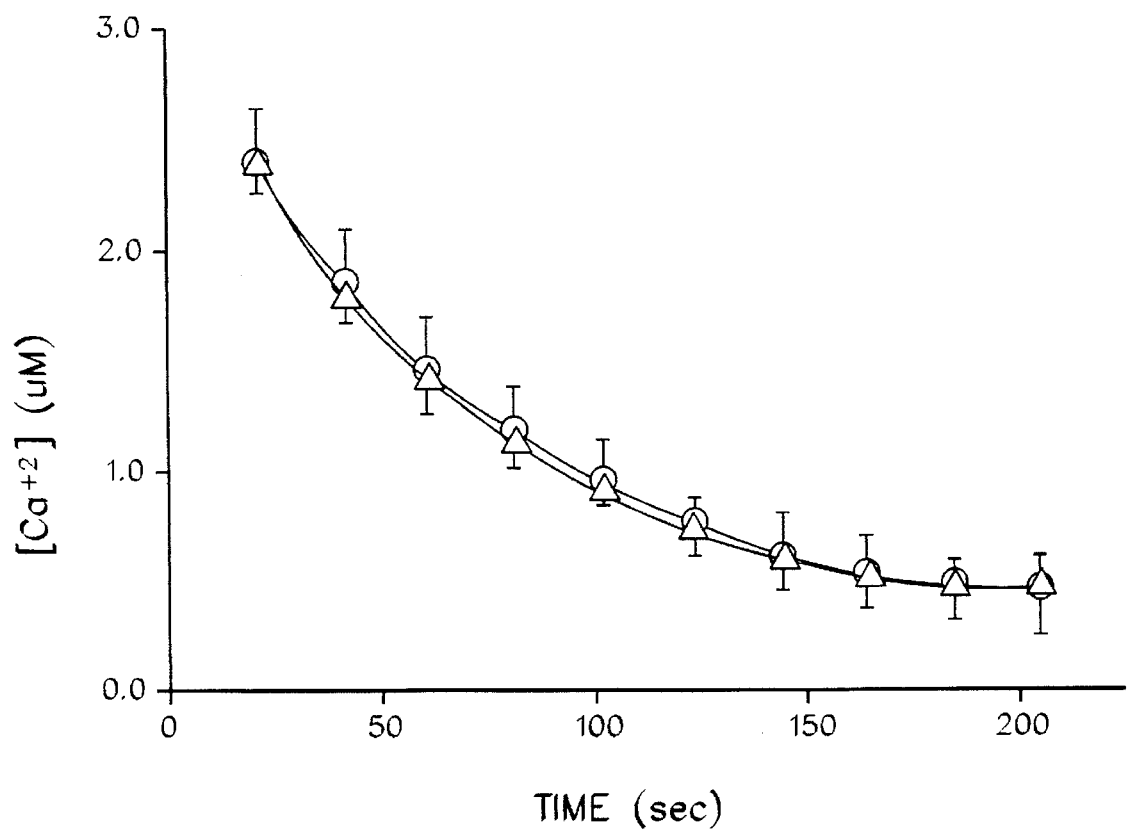
FIGS. 5A and 5B show the results of $Ca^{++}$ release studies. (A) The ATP-dependent SR $Ca^{++}$ uptake as determined by extravesicular fura-2 signals. Samples were from normal hamsters (o), and cardiomyopathic hamsters (Δ). (B) The time course of caffeine-induced change in $[Ca^{++}]_{SR}$ at two developmental stages. Samples were from normal hamsters at 30–40 days (o) and 200–300 days (Δ), and cardiomyopathic hamsters at 30–40 days (●) and 200–300 days (▲).

Fura-2 was also used to monitor ATP-dependent $Ca^{++}$ uptake by SR vesicles isolated from the cardiomyopathic and normal hamster hearts. Fura-2 acid (3 µM) was added outside the vesicles (5 µg) to buffer (2 ml) containing 500 µM ATP. Changes in fura-2 fluorescence resulted from the decline in free $Ca^{++}$ during active $Ca^{++}$ accumulation by the vesicles (Kargacin et al., *Am J. Physiol.* 245:1533 (1988)). FIG. 5a presents the $Ca^{++}$ uptake by SR from myopathic hearts (CM) and normal hearts (NH) at the prehypertrophic stage. As illustrated, the velocities of ATP-dependent $Ca^{++}$ uptake by isolated SR vesicles was similar at both developmental stages in SR vesicle preparations from myopathic and normal hearts.

Figure 5B:
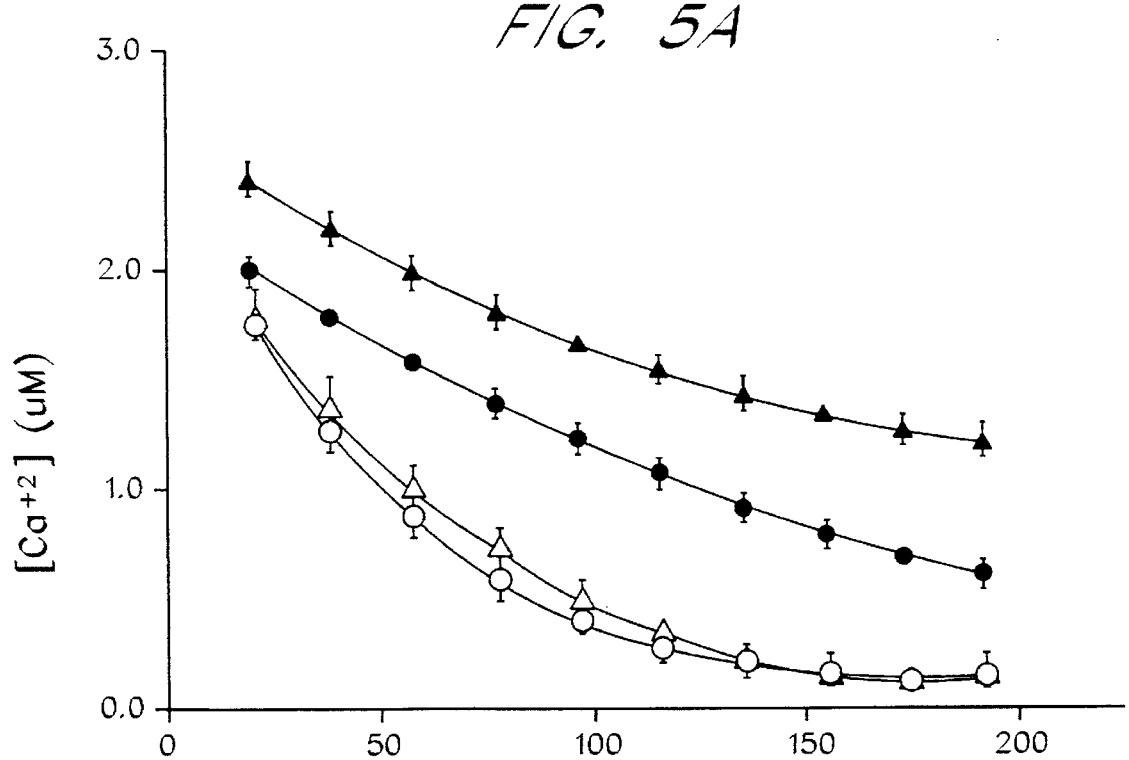

FIG. 5b shows the velocities of $Ca^{++}$ release estimated from the changes in the fura-2 fluorescence ratio produced by caffeine and ryanodine. Significantly, 20 mM caffeine-induced fluorescence ratio changes in fura-2 loaded SR vesicles isolated from cardiomyopathic hamster hearts (CM) at prehypertrophic and heart failure stages and age-matched normal hamster hearts (NH). The velocity of $Ca^{++}$ release by caffeine as judged by the intravesicular free $Ca^{++}$ signal was significantly reduced in myopathic SR vesicles compared to normal controls at both early and late heart failure stages. Similar results have been obtained using ryanodine. This abnormality in SR $Ca^{++}$ release, detectable at an early stage of this disease, may play an important role in contractile dysfunction. The decrease of SR $Ca^{++}$ release that accompanied normal SR $Ca^{++}$ uptake may contribute to SR $Ca^{++}$ overload at subsequent stages.

To gain further understanding of the mechanism underlying this abnormality in SR $Ca^{++}$ release function, single channel behavior of the SR $Ca^{++}$ release channel in the cardiomyopathic hamster heart was characterized at the prehypertrophic stage.

Example 7 describes the methods used to prove that the SR $Ca^{++}$ Release Channel was altered in prehypertrophic myocytes.

EXAMPLE 7

Abnormality of SR $Ca^{++}$ Release Channel in Prehypertrophic Myocytes

Figure 6A:
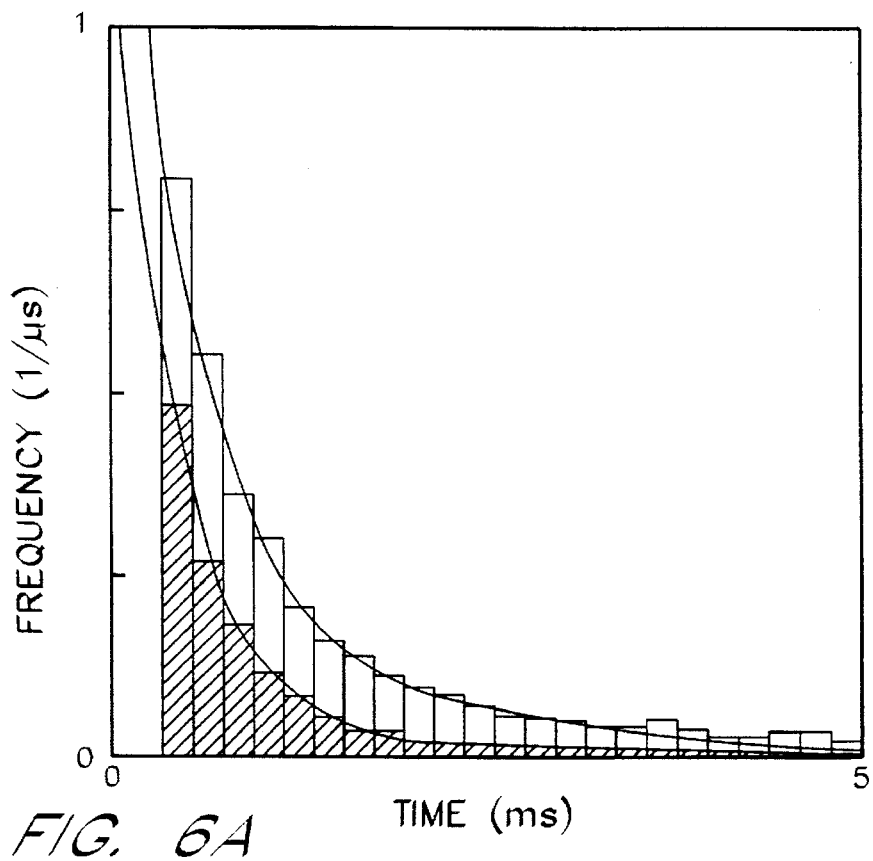
FIGS. 6A and 6B show the channel mean open time and channel mean closed time for normal and myopathic cells at the prehypertrophic stage. (A) Long closed times. Open bars represent normal myocytes; closed bars represent prehypertrophic myopathic myocytes. (B) Short closed times. Open bars represent normal myocytes; closed bars represent prehypertrophic myopathic myocytes.

Single $Ca^{++}$ release channels from vesicles of normal (FIB) and cardiomyopathic (Bio 14.6) cardiac junctional SR were incorporated into uncharged planar lipid bilayers according to the method described by Smith et al., in *J. Physiol* 88:573 (1986). The general characteristics of channels from normal hamsters were similar to those described previously in canine, sheep and rat cardiac SR membranes. Relevant data from this procedure is presented in FIG. 6a. As indicated, 100 µM $Ca^{++}$ and 1 mM ATP caused near maximal activation of one channel. Both ruthenium red and ryanodine had characteristic effects on the $Ca^{++}$ release channels as would be appreciated by one having ordinary skill in the art. In SR membranes from cardiomyopathic hearts at the prehypertrophic stage, the number of openings per unit time was clearly less than in age-matched normal controls. The appearance of individual openings was not significantly different at this time resolution. The decrease in open probability from $P_o$=0.03 in the normal hamster to $P_o$=0.01 in the cardiomyopathic hamster clearly appeared to be due to a decreased frequency of channel openings. In SR from cardiomyopathic hearts at the prehypertrophic stage, the number of openings was reduced and the duration and frequency of long closure was increased compared with that in SR from age-matched normal hearts. The differences in open probability between the normal and myopathic groups were revealed in channels exhibiting both random openings (5 µM $Ca^{++}$ in cis) and bursting channel activity (100 µM $Ca^{++}$ in cis) ($P_o$=0.20 in normal SR, n=15; $P_o$=0.08 in SR from prehypertrophic hearts, n=15).

Figure 6B:
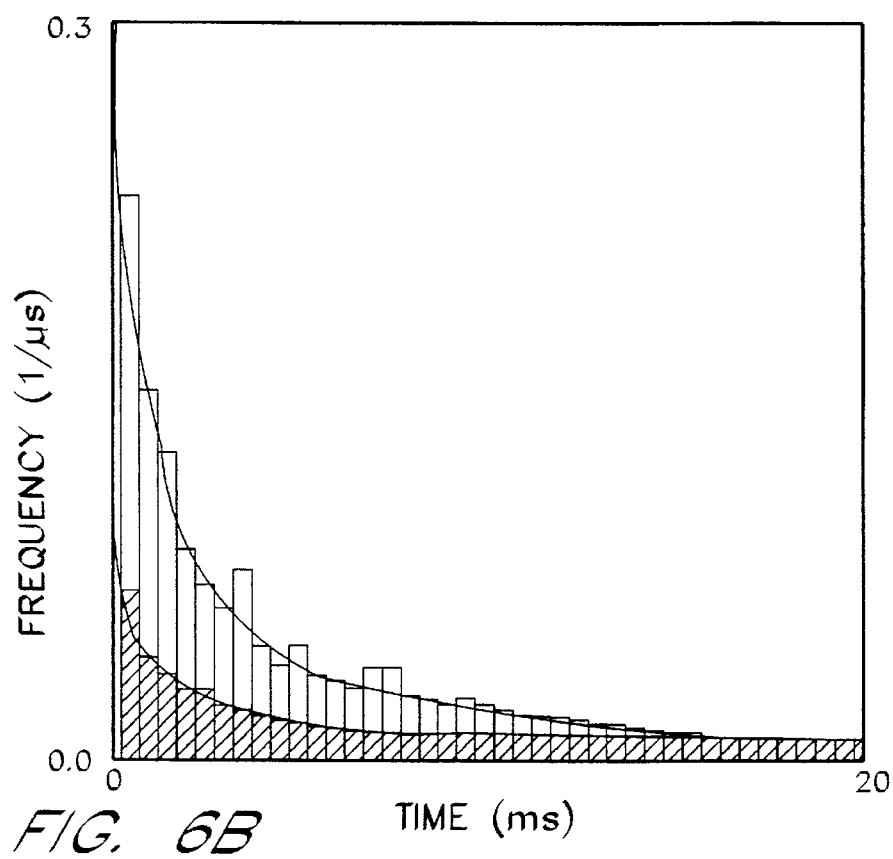

To quantitatively assess the characteristics of $Ca^{++}$ release channels in myopathic SR, a standard kinetic analysis of open and closed times on both random and bursting forms of channel gating was performed. As shown in the histograms of channel open times, FIG. 6b, the channel mean open times were not significantly different between the two groups. However, the areas of both exponential components were lower in SR $Ca^{++}$ release channels recorded from myopathic hearts when compared with those from normal hearts. There was no significant difference in two short closed times between two groups. The very slow closed time constant was significantly increased in recordings from the myopathic group. These findings indicated that the fewer openings were due to an increase in the proportion of long closed times which significantly contributed to the reduction in open probability on randomly gating $Ca^{++}$ release channel in cardiomyopathic hearts at the prehypertrophic stage. Similar results have been found in the bursting $Ca^{++}$ release channel. The significantly decreased number of channel openings without any change in duration in myopathic group was primarily due to prolonged long closures.

The $Ca^{++}$ release channel open probability in the activating and inhibiting $Ca^{++}$ concentration range has also been compared in the SR vesicles from Bio 14.6 hamster hearts at the prehypertrophic stage and from age-matched normal hamster hearts using the method described above. When $Ca^{++}$ concentration in cis was in the activating range, the concentration-response curve of relative channel open probability in SR from myopathic heart was significantly shifted to the right. With the $Ca^{++}$ concentration in the inhibiting range, the concentration-response curve was significantly shifted to the left. The area corresponding to the channel-active "window" was 67% decreased in prehypertrophic cells when compared with age-matched normal cells. This alteration was also found in hearts isolated from 15 to 18 day old prehypertrophic hamsters.

These findings provided direct evidence for a molecular alteration of the SR $Ca^{++}$ release channel in cardiomyopathic hamster myocytes. This abnormality was detected earlier than any other alteration which has been reported in this experimental system.

The molecular basis underlying this alteration could conceivably have been caused by abnormal structure or expression of the gene encoding the SR $Ca^{++}$ release channel. The levels of mRNA encoding the SR $Ca^{++}$ release channel were found to be normal in Bio 14.6 myopathic hearts at the prehypertrophic stage, but significantly reduced at the heart failure stage when compared with age-matched normal controls. Expression of the mRNAs encoding the $Na^+/Ca^{++}$ exchanger and dihydropyridine receptor were not significantly altered in myopathic hearts at any of the three developmental stages described herein. These results suggested that the altered expression of SR $Ca^{++}$ release channel may be responsible for the abnormal $Ca^{++}$ handling and contractile function in the cardiomyopathic hamster hearts at the heart failure stage.

Altered SR $Ca^{++}$ release channel mRNA expression was not likely responsible for the altered channel function in this genetic model given the evidence for alteration of SR $Ca^{++}$ channel provided by bilayer studies disclosed above. These latter data were consistent with altered structure of the SR $Ca^{++}$ release channel protein. It was, therefore, most likely that the molecular basis underlying the defect in Bio 14.6 hamsters was a mutated SR $Ca^{++}$ release channel gene. Accordingly, the genes encoding the Bio 14.6 and wild-type SR $Ca^{++}$ release channels were compared at the molecular level. More specifically, a restriction fragment length polymorphism (RFLP) analysis was carried out.

Example 8 describes the methods used to identify a difference between the structures of the SR $Ca^{++}$ release channel genes of hamsters that were normal controls or that were genetically predisposed to the development of cardiomyopathy.

EXAMPLE 8

RFLP Analysis: SR $Ca^{++}$ Release Channel Gene Structure in Bio 14.6 and Bio 53.58

Genomic DNA was prepared from normal (FIB) and cardiomyopathic (Bio 14.6 and Bio 53.58) hamster hearts. Tissue was rapidly frozen and crushed to produce readily digestible pieces. The processed tissue was placed in a solution of proteinase K and sodium dodecyl sulfate and incubated until most of the cellular protein was degraded. The digest was deproteinized by successive phenol/cloroform/isoamyl alcohol extractions, recovered by ethanol precipitation, dried and resuspended in TE buffer (Enrietto et al., *Cell* 35:369 (1983)).

Southern analysis was carried out according to standard methods. Briefly, 10 µg samples of genomic DNA were digested with 18 different restriction endonucleases and then separated by agarose gel electrophoresis. The restriction enzymes employed in this procedure were: EcoRI, BamHI, NciI, ApaI, KpnI, PstI, BssHII, MboI, BclI, NotI, DdeI, SpeI, AvaI, TaqI, ScaI, SacII, EcoRV and HindIII. The gels were then blotted to a nylon membrane. The SR $Ca^{++}$ release channel probe was random primed using a commercially available kit (Pharmacia). The cDNA encoding the human cardiac muscle ryanodine receptor used for this preliminary study was provided by Dr. A. Marks' laboratory. This cDNA probe, called HCRC1, corresponded to nucleotides 460–5440 of the cDNA encoding the rabbit cardiac release channel. After hybridization, the membrane was washed under standard high stringency conditions and exposed to X-ray film at −70° C. with an intensifying screen.

With the exception of HindIII digested DNA samples, all restriction enzyme digests gave rise to bands that were identical in DNA samples derived from cardiomyopathic hamster hearts and normal control hearts. However, hybridization of the HCRC1 probe to HindIII digested genomic DNA revealed a 4 kb band in normal hearts and an additional 1.9 kb band in both Bio 14.6 and Bio 53.58 cardiomyopathic hearts. Significantly, both Bio 14.6 and Bio 53.58 animals are genetically predisposed to cardiomyopathy.

Thus, the results presented above indicated that HindIII digestion of genomic DNA isolated from Bio 14.6 or Bio 53.58 hamsters could be used to identify an RFLP that correlated with inheritance of idiopathic dilated cardiomyopathy. Whether the same inherited gene structure would also characterize humans who were predisposed to cardiomyopathy remained to be demonstrated. This was particularly relevant, because the human SR $Ca^{++}$ release channel has recently been cloned and sequenced by Tunwell et al., (*Biophysical Journal* 68:A52 (1995)), and has been shown to be 98.6% similar, at the amino acid level, to the rabbit homolog.

Accordingly, we investigated whether a similar RFLP, as identified in the animal model, would characterize the human SR calcium release channel receptor gene of humans afflicted with idiopathic dilated cardiomyopathy. Although human cardiac myocytes originally served as the source of DNA in these studies, it was subsequently discovered that genomic DNA isolated from other body tissues could similarly be used with equally good results. For example, genomic DNA isolated from peripheral blood lymphocytes could serve as a source of genomic DNA that can be tested for the presence of the genetic indicator of susceptibility to idiopathic dilated cardiomyopathy.

Example 9 describes the methods used to identify an RFLP that was associated with idiopathic dilated cardiomyopathy in humans.

EXAMPLE 9

Correlation Between an RFLP in the Human SR $Ca^{++}$ Release Channel Gene and Idiopathic Dilated Cardiomyopathy Genomic DNA was isolated from human ventricular tissue samples according to standard procedures. Samples were from 4 disease-free organ donors and 40 patients having end-stage heart failure. These patients were undergoing cardiac transplant surgery at UCLA Medical Center at the time the experiment was carried out. Among the subjects were 19 patients having idiopathic dilated cardiomyopathy, and 21 having coronary artery disease (ischemic cardiomyopathy). Additionally, genomic DNA was extracted from blood samples taken from 171 normal controls.

All DNA samples were separately digested with a battery of restriction enzymes, electrophoresed (5 µg/lane) on agarose gels and blotted to nylon membranes (Quiagen) essentially as described by Reed et al., in *Nucleic Acids Res.* 13:7207 (1985). The enzymes employed in this procedure were: EcoRI, BamHI, NciI, ApaI, KpnI, PstI, BssHII, MboI, BclI, NotI, DdeI, SpeI, AvaI, TaqI, ScaI, SacII, EcoRV and HindIII. The membranes were then hybridized to a radiolabeled DNA probe representing a segment of the Human Cardiac Release Channel 1 (HCRC1) cDNA. This cDNA probe corresponded to nucleotides 4460–5440 of the rabbit cardiac $Ca^{++}$ release channel cDNA (Brillantes et al., *Circulation Research* 71:18 (1992)), and was synthesized alternatively by nick translation or random priming with equally good results. Following hybridization and washing under high stringency conditions, all according to standard protocols, the membranes were air dried and autoradiographed.

Comparison of the Southern blotting results indicated that HindIII digestion gave rise to a 3.7 kb fragment that was present in 18/19 patients with idiopathic dilated cardiomyopathy, but only in 1/21 patients with ischemic cardiomyopathy. Significantly, this 3.7 kb band was not present in samples of HindIII digested DNA isolated from the 4 normal controls. This 3.7 kb DNA fragment was also found in genomic DNA extracted from blood cells in 6/171 normal controls. No differences were found between idiopathic dilated cardiomyopathy or ischemic cardiomyopathy patients and normal controls by RFLP analysis using any of the other restriction enzymes. These results are summarized in Table 1.

TABLE 1

Frequency of the 3.7 kb RFLP in Genomic DNA from Various Sources

| Features of Tissue Source | Positive | Negative |
|---|---|---|
| Idiopathic Dilated Cardiomyopathy | 18 | 1 |
| Ischemic Cardiomyopathy | 1 | 20 |
| Myocardium from normal controls | 0 | 4 |
| Blood cells from normal controls | 6 | 165 |

These results confirmed that an RFLP, represented by a 3.7 kb DNA fragment, distinguished normal and cardiomyopathic humans and could be detected by Southern blotting. More specifically, the HCRC1 cDNA probe identified a 3.7 kb band in Southern blotted genomic DNA from individuals afflicted with idiopathic dilated cardiomyopathy. Thus, we had identified a genetic feature that occurred with very high frequency in the population of patients afflicted with idiopathic dilated cardiomyopathy. This 3.7 kb band was absent from the digests of genomic DNA isolated from control individuals. This finding led us to investigate the nature of the mutation that gave rise to the RFLP.

Example 10 describes the method used to identify the mutation within the SR $Ca^{++}$ release channel gene that produced the 3.7 kb RFLP associated with idiopathic dilated cardiomyopathy.

EXAMPLE 10

DNA Sequence Analysis of the Mutation

HindIII digested genomic DNA isolated from patients afflicted with idiopathic dilated cardiomyopathy was size fractionated on 0.8% agarose. A GENE-CLEAN KIT (BIO 101) was used to purify DNA from the region of the gel having DNA fragments 3.7 kb in length. These fragments were subsequently cloned into the pUCNC vector using the PCR-CLONING SYSTEM (5'-3' Inc.). A colony hybridization protocol using radiolabeled HCRC1 probe was used to identify clones harboring the desired fragments. Dideoxy nucleotide sequencing of the cloned 3.7 kb fragment was performed using SEQUENASE 2.0 (U.S. Biochemical) and $[\alpha^{35}S]dATP$ (Amersham and DuPont-NEN). To produce all of the necessary sequencing templates, unidirectional deletions were prepared using the ERASE-A-BASE system from Promega.

The cloned fragment was found to correspond to nucleotides 4650–8760 of the cDNA encoding the human cardiac $Ca^{++}$ release channel reported by Tunwell et al., in *Biophysical Journal* 68:A52 (1995). Significantly, a point mutation was discovered in 10/10 patients with idiopathic dilated cardiomyopathy. In all 10 patients studied, Codon 8258 was mutated from AGG to AAG, resulting in an amino acid change from arginine to lysine. In one patient, there was a missense mutation at codon 8634 that resulted in an amino acid change from glutamine to histidine. There were also a nonsense mutation in 3 patients.

These results indicated that all 10 of the patients with idiopathic dilated cardiomyopathy possessed SR $Ca^{++}$ release channel genes having point mutations at positions corresponding to nucleotides 8366 and 8762 of the rabbit cDNA sequence described by Otsu et al., in *J. Biol Chem.* 265:13472 (1990). The mutation at position 8762 created a HindIII site that was responsible for the 3.7 kb RFLP and that provided one of the sticky ends used for cloning the fragment in the above procedure. Thus, the presence of either of the two mutations identified above correlated with the idiopathic dilated cardiomyopathy phenotype. Based on these findings, we proceeded to create a diagnostic test that could be used to identify individuals harboring the mutation that correlated with this disease.

As indicated above, all 10 of the 3.7 kb HindIII RFLP fragments cloned from the genomic DNA of patients with idiopathic dilated cardiomyopathy shared the same termini. This indicated that all patients having the RFLP had the same HindIII site at a position corresponding to nucleotide 8762 of the rabbit SR $Ca^{++}$ release channel gene. Since the cloned 3.7 kb DNA fragments were all derived from patients having idiopathic dilated cardiomyopathy, it remained to be determined whether patients having ischemic cardiomyopathy also would have the same genetic mutation within this region of the SR $Ca^{++}$ release channel gene.

As disclosed in the following Example, a simple PCR protocol was employed to amplify a genomic DNA fragment that encompassed the region of the SR $Ca^{++}$ release channel gene that distinguished the normal and the idiopathic dilated cardiomyopathy genotypes. More specifically, oligonucleotide primers were selected for use in a procedure that would amplify the genomic DNA which flanked both mutations within the human gene that corresponded to nucleotides 8366 and 8762 of the rabbit cDNA homolog. Both of these mutations were identified in the DNA of patients with idiopathic dilated cardiomyopathy, but were absent from the DNA of normal controls. The following Example discloses results related to the presence of these mutations in the DNA of patients afflicted with a second form of cardiomyopathy.

Example 11 describes the methods used to determine whether genomic DNA encoding the SR $Ca^{++}$ release channel gene of patients with ischemic cardiomyopathy exhibited the same mutation we had identified in patients afflicted with idiopathic dilated cardiomyopathy.

EXAMPLE 11

Sequence Analysis of PCR-Amplified DNA Products from Genomic DNA of Patients with Ischemic Cardiomyopathy Genomic DNA was isolated from ventricular muscle tissue of patients diagnosed with ischemic cardiomyopathy according to standard laboratory procedures. Oligonucleotide primers having the sequences 5'-TTCAAACTGGCACTGCCTTGCCTGAGTGCCGTTGC-3' (SEQ ID NO:1) and 5'-AAGTTTGCAGAATAGGCTAGTCACCATTTC-3' (SEQ ID NO:2) were used as primers in a standard PCR protocol. These primers corresponded to nucleotides 7987–8021 and 9007–9036 of the rabbit SR $Ca^{++}$ release channel gene, respectively. Conditions used in the PCR amplification included 35 cycles of: 90° C. for 30 seconds, 42° C. for 30 seconds and 70° C. for 60 seconds. The buffer used in the amplification procedure has been described by Sidransky et al., in *Science* 252:706 (1991). The ~1.1 kb amplification products were cloned into T-tailed plasmid vectors using the PCR CLONING SYSTEM from 5'-3', Inc. The cloned inserts were then sequenced using a modified T7 DNA polymerase (U.S. Biochemical). The nucleotide sequence of the amplified and cloned human SR $Ca^{++}$ release channel gene segments produced using DNA templates obtained from ischemic cardiomyopathy patients were all identical to each other. The nucleotide sequence of the cloned DNA fragment derived from patients having ischemic cardiomyopathy is presented as SEQ ID NO:3.

Significantly, an identical sequence was obtained when the DNA templates employed in the amplification procedure were obtained from normal control individuals. In contrast, polynucleotides having the sequence of SEQ ID NO:4 were obtained when DNA templates from individuals afflicted with idiopathic dilated cardiomyopathy were employed in the amplification procedure.

Results of this analysis indicated that the sequences of the SR $Ca^{++}$ release channel genes of patients having ischemic cardiomyopathy and idiopathic dilated cardiomyopathy differed at only two positions. These point mutations, which occurred at positions 380 and 776 of the sequences presented as SEQ ID NO:3 and SEQ ID NO:4, corresponded to positions 8366 and 8762 of the rabbit cDNA sequence disclosed by Otsu et al., in *J. Biol Chem.* 265:13472 (1990). Notably, the DNA sequence of the fragments amplified using ischemic cardiomyopathic patients' genomic DNA as a template precisely matched the sequence that was obtained when the starting DNA templates were from normal controls. Thus, only genomic DNA isolated from individuals afflicted with idiopathic dilated cardiomyopathy contained point mutations in the SR $Ca^{++}$ release channel gene at the two locations indicated above. Accordingly, any technique that detects either of the two mutant nucleotides disclosed herein can be adapted to a diagnostic test for genetic susceptibility to idiopathic dilated cardiomyopathy.

Two particularly successful approaches have been used to detect the inherited genetic markers that are diagnostic of susceptibility to idiopathic dilated cardiomyopathy. The first approach involved DNA sequence analysis to determine whether a patient's DNA sample contained either an adenosine residue at position 380, or a thymidine residue at position 776 of the SR $Ca^{++}$ release channel gene segment represented by the wild-type DNA sequence of SEQ ID NO:3. As will be apparent from the preceding disclosure, these two nucleotide positions represent the differences that distinguish the SR $Ca^{++}$ release channel gene segments represented by SEQ ID NO:3 and SEQ ID NO:4. When either mutation was present in the patient's DNA sample, the patient was identified as at-risk for idiopathic dilated cardiomyopathy. Those having ordinary skill in the art will appreciate that the sequence of only a subset of the nucleotides of SEQ ID NO:3 or SEQ ID NO:4 must be obtained to determine whether either of the relevant mutations is present in a DNA sample.

A simplified testing method has been used to detect a HindIII site that is only present in the SR $Ca^{++}$ release channel gene of individuals at risk of developing idiopathic dilated cardiomyopathy. More specifically, HindIII digestion of an amplified DNA segment representing a portion of the SR $Ca^{++}$ release channel gene has been used to probe for one of the two mutations that correlated with disease susceptibility. According to this method, cleavage of an amplification product that encompassed the position corresponding to the HindIII site within a DNA fragment represented by the sequence of SEQ ID NO:4 indicated the presence of the mutation that correlated with susceptibility to idiopathic dilated cardiomyopathy. In the event that the HindIII restriction endonuclease failed to cleave the amplification product, DNA sequencing of that amplification product could be carried out to verify the absence of the mutation that conferred susceptibility to idiopathic dilated cardiomyopathy. Such a procedure would provide one means of ensuring against false negative results.

Example 12 describes an assay for detecting a HindIII cleavage site that was diagnostic of idiopathic dilated cardiomyopathy.

EXAMPLE 12

Genetic Test for Idiopathic Dilated Cardiomyopathy

Genomic DNA was extracted from tissues of 10 idiopathic dilated cardiomyopathy patients, 4 ischemic cardiomyopathy patients and 4 normal controls according to standard procedures. The 10 idiopathic dilated cardiomyopathy patients used in this Example represented 10 of the 18 individuals who possessed the 3.7 kb RFLP in the procedure of Example 9. Cardiac myocytes served as the tissue source for genomic DNA isolated from the cardiomyopathy patients while peripheral blood lymphocytes served as the source of DNA for the normal control samples. A fragment of genomic DNA corresponding to the span from 7987 to 9036 of the rabbit SR $Ca^{++}$ release channel gene was amplified by a PCR protocol that employed two oligonucleotide primers having the sequences of SEQ ID NO:1 and SEQ ID NO:2. Genomic DNA samples (100 ng) were used as templates in 25 µl reactions that contained 10 mM Tris-HCl (pH 8.3), 50 mM KCl, 0.75 mM $MgCl_2$, 0.01% gelatin, 200 µM dNTPs, 1 µM each oligonucleotide primer and 5 units of Taq DNA polymerase. PCR conditions consisted of 35 cycles of 95° C. for 30 seconds, 42° C. for 30 seconds, and 70° C. for 60 seconds. These procedures resulted in the amplification of a DNA fragment of approximately 1.1 kb in length, that included both of the positions (8366 and 8762) of the SR $Ca^{++}$ release channel gene demonstrated to be mutated in idiopathic dilated cardiomyopathy patients. Samples of the amplification products were subsequently digested with HindIII and electrophoresed on 1% agarose gels according to standard procedures. At the conclusion of electrophoresis, the gels were stained with ethidium bromide, placed on an ultraviolet transilluminator and photographed to reveal the sizes of the various DNA fragments.

Results from this procedure indicated that only the amplification products derived from samples of genomic DNA obtained from patients having idiopathic dilated cardiomyopathy possessed an internal HindIII cleavage site. The amplification products in the lanes of the gel corresponding to normal control and ischemic cardiomyopathy patients had lengths of approximately 1.1 kb, and were not changed by HindIII digestion. Thus, none of these DNA fragments possessed an internal HindIII site. Conversely, HindIII digestion of all 10 amplified DNA samples representing the genomic DNA of idiopathic dilated cardiomyopathy patients led to altered fragment sizes. More specifically, in all 10 samples HindIII digestion eliminated the 1.1 kb band and produced bands of approximately 0.8 and 0.3 kb. This indicated that all of the DNA fragments amplified from the idiopathic dilated cardiomyopathy patients' genomic DNA samples contained internal HindIII sites.

Significantly, there were neither false positive nor false negative results using the above procedure. Only individuals who were identified as having idiopathic dilated cardiomyopathy, and who were shown to possess the 3.7 kb RFLP in Example 9, were shown to have amplification products having internal HindIII cleavage sites. This confirmed the utility and accuracy of the invented diagnostic test.

To illustrate the generality of this method, we repeated the above procedure using a different primer set and obtained identical results. More specifically, the PCR amplification reaction was performed using primers having the sequences 5'-ATAATTCCTGAGAAGTTGGAATACTTCATT-3' (SEQ ID NO:5) and SEQ ID NO:2. This primer set amplified a polynucleotide 0.9 kb in length. The sequence of the amplification product that resulted from the use of a genomic DNA template obtained from an individual afflicted with idiopathic dilated cardiomyopathy is presented as SEQ ID NO:6. Notably, nucleotide positions 230 and 626 of this amplification product represented the two nucleotides that were diagnostic of idiopathic dilated cardiomyopathy. HindIII cleavage of the polynucleotide represented by the sequence of SEQ ID NO:6 resulted in cleavage products of approximately 0.6 kb and 0.3 kb. Thus, those having ordinary skill in the art will appreciate that a many different primer sets can be used to amplify segments of the SR $Ca^{++}$ release channel gene that encompass either or both of the nucleotide positions disclosed to identify individuals at risk of idiopathic dilated cardiomyopathy. The products of those amplification reactions can then be used in DNA sequencing protocols or HindIII cleavage protocols, as described above, to create a diagnostic test for idiopathic dilated cardiomyopathy.

In addition to the nucleic acid based diagnostic assays disclosed above, those having ordinary skill in the art will appreciate that alternative assays based on detection of the wild-type and mutant forms of the SR $Ca^{++}$ release channel receptor protein will also be useful. For example, we anticipate the production of monoclonal antibodies having specificities for the SR $Ca^{++}$ release channel receptor epitope corresponding to the protein domain that includes the codon represented by the mutation identified in patients having ischemic cardiomyopathy. Such antibodies will be useful diagnostic reagents.

Example 13 describes an immunohistochemical test that can be used to identify individuals at risk of developing idiopathic dilated cardiomyopathy.

EXAMPLE 13

An Immunohistochemical Test for Idiopathic Dilated Cardiomyopathy

An antigenic composition comprising a segment of the SR $Ca^{++}$ release channel representing the domain of the protein that is mutant in idiopathic dilated cardiomyopathy is first prepared. The composition is likely a fusion protein, but may also be a synthetic peptide and may be coupled to a carrier for improved antigenicity. A monoclonal antibody, or variant thereof, having binding specificity for the mutant form of the SR $Ca^{++}$ release channel is next prepared according to methods that will be appreciated by those having ordinary skill in the art. The mutant-binding antibody can specifically bind the mutant form of the receptor without binding the wild-type receptor.

An identical procedure is used to prepare a monoclonal antibody that can specifically bind the wild-type form of the SR $Ca^{++}$ release channel. The wild-type-binding antibody can specifically bind the wild-type form of the receptor without binding the mutant form.

A tissue sample containing cardiac myocytes is obtained by standard methods from an individual to be tested for genetic susceptibility to idiopathic dilated cardiomyopathy. The method of obtaining the myocytes may involve the use of a catheter. The sample is next prepared for analysis by immunohistology using the two antibody preparations as reagents. If the wild-type-binding antibody stains the tissue sample, the tissue donor is either not susceptible, or is an unaffected carrier of the trait conferring susceptibility to idiopathic dilated cardiomyopathy. If the mutant-binding antibody stains the tissue sample, and the wild-type-binding antibody does not stain, the tissue donor is susceptible to idiopathic dilated cardiomyopathy.

This immunohistological assay represents yet another method that can be used in a diagnostic procedure for identifying individuals susceptible to idiopathic dilated cardiomyopathy.

We also believe that the mutant form of the SR $Ca^{++}$ release channel disclosed herein is useful in assays to identify candidate therapeutic agents for the treatment of idiopathic dilated cardiomyopathy. More specifically, we anticipate that drugs which cause the mutant SR $Ca^{++}$ release channel to behave like the wild-type channel are candidates for the treatment of idiopathic dilated cardiomyopathy. We believe that these anticipated drugs will increase the amount of calcium released from the SR in the excitation-contraction coupling process. This would effectively increase the myocardium contraction.

Example 14 describes in vitro methods that can be used to identify drugs that cause mutant SR $Ca^{++}$ release channels to behave like wild-type channels. Drugs identified by the following method can then be tested in vivo as therapeutics by methods well known to those of ordinary skill in the art for effectiveness in the treatment of idiopathic dilated cardiomyopathy.

EXAMPLE 14

Drug Discovery Using Mutant SR $Ca^{++}$ Channel Protein

Myocardial SR is fractionated into heavy, intermediate, and light density vesical fractions by differential and sucrose gradient centrifugation as described previously. Heavy SR membranes containing the $Ca^{++}$ release channel are recovered from the 36-45% region of a sucrose gradient that contained myocardium membranes.

Mulle-Rudin planar bilayer containing phosphatidytanoylphosphatidylcholine (10 mg/ml) in decane is painted across a 200 μm hole in a Lexan cup inserted into a cut-away PVC block. In all experiments, the cis chamber is defined as the side to which SR vesicles are added; the opposite side is referred to as the trans chamber. All additions of $Ca^{++}$, $Mg^{++}$, EGTA or adenine nucleotides are made to the cis chamber. Applied voltages are defined with respect to the trans chamber held at virtual ground and therefore agree with the normal cellular convention. The cis chamber, inside the Lexan cup contains 0.25M choline Cl, 5 mM $CaCl_2$, 100 μM EGTA, 10 mM Tris HEPES, pH 7.4 and the trans chamber contains 50 mM choline Ca, 5 mM $CaCl_2$, 100 μEGTA, 10 mM Tris HEPES, pH 7.4. Heavy SR vesicles in 0.3M sucrose, 10 mM K Pipes (1,4-piperazinediethanesulfonic acid), pH 7.0, are added to the cis chamber and stirred (final protein concentration, 3 μg/ml). Shortly after vesicle addition, step-like vesicle-bilayer fusion events are observed. The resulting conductances are characteristic of a cation-conducting pathway with an equilibrium reversal potential of +25 mV. After vesicle-bilayer fusion, both chambers are perfused to remove any permeate anions and unfused vesicles. The trans chamber is perfused with 3 vol of 52 mM Tris/HEPES, (pH 7.4). During the perfusion step, buffer is pumped into the bottom of each chamber via a small Tygon hose and simultaneously withdrawn through a hose positioned at the top of the chamber. The density of the HEPES perfusion buffer is greater than that of the choline Cl solution so that during perfusion the choline Cl is effectively displaced by the HEPES solution. The experiments are conducted at room temperature (22°–24° C.).

Single channel currents are recorded and voltage control is imposed with a commercial patch clamp unit (Axon Instruments, Foster City, Calif.). The data is acquired in real time and filtered at a cut-off frequency of 100 Hz with an 8-pole Beisel filter, digitized at 500 Hz and stored for analysis. The ionic currents are subjected to conventional single channel analysis, carried out using the pCLAMP software system (Axon Instruments, Foster City, Calif.) and custom programs. The analysis can be started with amplitude histograms to determine the single channel conductance. Once the average single channel current is determined, opening and closing transitions can be detected using as threshold criterion a level equal to 0.5 of the predominant open channel current. This is followed by determination of event durations, construction of open time histograms, and computation of open probability as the fraction of the total pulse duration occupied by open events. When two open events superimpose their currents, their durations are independently added for calculation of open probability. In addition to single channel analysis, ensemble of ionic currents obtained with pulses to the same voltage is averaged. Typically, one stable channel in a bilayer could be subjected to between 50 and 300 pulses, covering from one to five different test voltages. From 50 to 150 sweeps are obtained per voltage level, per bilayer. The voltage dependence of channel open probability and the time dependence of averaged currents is fitted with theoretical functions using nonlinear least-squares routines which can be calculated using a standard error of the parameter estimates.

Using this approach, SR $Ca^{++}$ channel gating properties can be measured and compared. Channel gating properties include the single channel open probability, open and close lifetime, single channel current voltage relation and channel kinetics. These properties can be compared between vesicles from normal organ donors and the heavy SR vesicles from myocardium of patients with end-stage heart failure caused by various cardiomyopathies Drugs to be tested for their effects on SR $Ca^{++}$ release channel properties can be added to the cis chamber for bilayers that incorporate vesicles obtained from cardiomyopathic myocytes. Readings can be obtained before and after drug addition. Drugs that cause SR $Ca^{++}$ release channels from cardiomyopathic myocytes to exhibit properties similar to SR $Ca^{++}$ release channels isolated from normal control myocytes are candidates as therapeutic agents in the treatment of idiopathic dilated cardiomyopathy.

---

What is claimed is:

1. An isolated polynucleotide encoding a mutant human SR Ca$^{++}$ release channel, said polynucleotide consisting of the sequence of SEQ ID NO:3 with the exception of having nucleotide positions 380 and 776 substituted by residues other than guanosine.

2. The isolated polynucleotide of claim 1, wherein nucleotide position 380 is substituted by adenosine.

3. The isolated polynucleotide of claim 1, wherein nucleotide position 776 is substituted by thymidine.

4. A method of identifying an individual genetically predisposed to idiopathic dilated cardiomyopathy, comprising the steps of:
  (a) obtaining a tissue sample from the individual;
  (b) obtaining a population of polynucleotides from the tissue sample;
  (c) determining if the population includes a polynucleotide having the sequence of SEQ ID NO:3 except with a substitution at either position 380 or 776;
  (d) identifying said individual as being genetically predisposed to idiopathic dilated cardiomyopathy if said polynucleotide is present.

5. The method of claim 4, wherein the tissue sample is a sample of blood or a sample of cardiac myocytes.

6. The method of claim 4, wherein the determining step comprises PCR amplification.

7. The method of claim 4, wherein the determining step comprises DNA sequencing.

8. The method of claim 4, wherein the determining step comprises identifying a substitution of adenosine at position 380 of SEQ ID NO:3 or a substitution of thymidine at position 776 of SEQ ID NO:3.

9. The method of claim 4, wherein the determining step comprises cleavage by a restriction endonuclease followed by electrophoresis.

10. The method of claim 9, wherein the restriction endonuclease is HindIII, and wherein cleavage results in the formation of two polynucleotide fragments.

11. The method of claim 10, wherein said two polynucleotide fragments have lengths of from between about 300 and 800 base pairs.

12. The method of claim 4, wherein the determining step comprises identifying a 3.7 kb HindIII restriction fragment length polymorphism, wherein the presence of said fragment indicates the presence of said polynucleotide.

13. A diagnostic kit for detecting genetic susceptibility to idiopathic dilated cardiomyopathy, comprising:
  a pair of oligonucleotide primers for amplifying a segment of the SR Ca$^{++}$ release channel gene, a first of said pair being homologous to a sequence contained within SEQ ID NO:4 on one side of a HindIII restriction endonuclease cleavage site at position 777 of the sequence of SEQ ID NO:4, and a second of said pair being homologous to a sequence contained within SEQ ID NO:4 on another side of said HindIII restriction endonuclease cleavage site; and
  a HindIII restriction endonuclease for cleaving a polynucleotide amplified in a polymerase chain reaction conducted using said pair of oligonucleotide primers as reagents.

14. The diagnostic kit of claim 13, wherein the sequences of the primer are the sequences of SEQ ID NO:1 and SEQ ID NO:2.

15. The diagnostic kit of claim 13, wherein the sequences of the primer are the sequences of SEQ ID NO:5 and SEQ ID NO:2.

* * * * *